United States Patent
Sherman et al.

(10) Patent No.: US 6,312,612 B1
(45) Date of Patent: Nov. 6, 2001

(54) APPARATUS AND METHOD FOR MANUFACTURING AN INTRACUTANEOUS MICRONEEDLE ARRAY

(75) Inventors: Faiz Feisal Sherman; Vadim Vladimirovich Yuzhakov; Vladimir Gartstein, all of Cincinnati, OH (US); Grover David Owens, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/328,946

(22) Filed: Jun. 9, 1999

(51) Int. Cl.[7] .................................................. B81C 1/00
(52) U.S. Cl. .............................. 216/2; 216/11; 216/41; 216/56; 216/67; 216/79
(58) Field of Search ....................... 216/2, 11, 41, 216/56, 67, 79

(56) References Cited

U.S. PATENT DOCUMENTS

| | | | |
|---|---|---|---|
| 3,964,482 | 6/1976 | Gerstel et al. | 128/260 |
| 4,381,963 | 5/1983 | Goldstein et al. | 156/245 |
| 4,585,991 | * 4/1986 | Reid et al. | 216/2 |
| 4,784,737 | 11/1988 | Ray et al. | 204/180.1 |
| 5,156,591 | 10/1992 | Gross et al. | 604/20 |
| 5,250,023 | 10/1993 | Lee et al. | 604/20 |
| 5,256,360 | 10/1993 | Li | 264/219 |
| 5,279,544 | 1/1994 | Gross et al. | 604/20 |
| 5,318,557 | 6/1994 | Gross | 604/891.1 |
| 5,362,307 | 11/1994 | Guy et al. | 604/20 |
| 5,498,235 | 3/1996 | Flower | 604/20 |
| 5,527,288 | 6/1996 | Gross et al. | 604/140 |
| 5,551,953 | 9/1996 | Lattin et al. | 604/20 |
| 5,591,139 | 1/1997 | Lin et al. | 604/264 |
| 5,611,806 | 3/1997 | Jang | 606/167 |
| 5,658,515 | 8/1997 | Lee et al. | 264/219 |
| 5,681,580 | 10/1997 | Jang et al. | 424/449 |
| 5,704,520 | 1/1998 | Gross | 222/334 |
| 5,711,761 | 1/1998 | Untereker et al. | 604/20 |
| 5,730,714 | 3/1998 | Guy et al. | 604/20 |
| 5,735,273 | 4/1998 | Kurnik et al. | 128/635 |
| 5,771,890 | 6/1998 | Tamada | 128/635 |
| 5,800,420 | 9/1998 | Gross et al. | 604/890.1 |
| 5,807,375 | 9/1998 | Gross et al. | 604/890.1 |
| 5,814,020 | 9/1998 | Gross | 604/41 |
| 5,820,622 | 10/1998 | Gross et al. | 604/890.1 |
| 5,827,183 | 10/1998 | Kurnik et al. | 600/345 |
| 5,848,990 | 12/1998 | Cirelli et al. | 604/136 |
| 5,848,991 | 12/1998 | Gross et al. | 604/140 |
| 5,855,801 | 1/1999 | Lin et al. | 216/2 |

FOREIGN PATENT DOCUMENTS

| | | | |
|---|---|---|---|
| 1667864 | 3/1989 | (SU) . | |
| WO 96/37256 | 11/1996 | (WO) | A61N/1/30 |
| WO 97/03718 | 2/1997 | (WO) | A61M/37/00 |
| WO 97/48440 | 12/1997 | (WO) | A61N/1/30 |

(List continued on next page.)

OTHER PUBLICATIONS

Henry, McAllister, Allen & Prausnitz, Georgia Institute of Technology, Atlanta, GA *Micromachined Needles for the Transdermal Delivery of Drugs.*

(List continued on next page.)

*Primary Examiner*—Anita Alanko
(74) *Attorney, Agent, or Firm*—Bart S. Hersko

(57) ABSTRACT

A microneedle array is constructed of silicon and silicon dioxide compounds using MEMS (i.e., Micro-Electro-Mechanical-Systems) technology and standard microfabrication techniques. The microneedle array may be fabricated from a silicon die which can be etched in a microfabrication process to create hollow cylindrical individual microneedles. The resulting array of microneedles can penetrate with a small pressure through the stratum corneum of skin (including skin of animals, reptiles, or other creatures—typically skin of a living organism) to either deliver drugs or to facilitate interstitial fluid sampling through the hollow microneedles.

7 Claims, 18 Drawing Sheets

FOREIGN PATENT DOCUMENTS

| | | | |
|---|---|---|---|
| WO 97/48442 | 12/1997 | (WO) | A61N/1/30 |
| Wo 97/48441 | 12/1997 | (WO) | A61N/1/30 |
| WO 98/00193 | 1/1998 | (WO) | A61M/31/00 |
| WO 99/00155 | 1/1999 | (WO) | A61M/5/32 |
| WO 99/29298 | 6/1999 | (WO) | A61K/9/00 |
| WO 99/29364 | 6/1999 | (WO) | A61M/37/00 |
| WO 99/29365 | 6/1999 | (WO) | A61M/37/00 |

OTHER PUBLICATIONS

Sebastian Henry, Devin V. McAllister, Mark G. Allen, Mark R. Prausnitz, Georgia Institute of Technology, Atlanta, GA *Microfabricated Microneedles: A Novel Approach to Transdermal Drug Delivery*, Journal of Pharmaceutical Sciences vol. 87, No. 8, Aug. 1998, pp. 922–925.

Kyoseok Chun, Gen Hashiguchi, Hiroshi Toshiyoshi, Hiroyuki Fujita, The University of Tokyo *An Array of Hollow Microcapillaries for the Controlled Injection of Genetic Materials into Animal/Plat Cells.*

Advertisement for Glucowatch™, Cygnus, Inc.

Interview description of Glucowatch™ by Dr. Ronald Kurnik, Cygnus, Inc.

Sietse E. Wouters, Steven M. Dinh *Microelectrochemical Systems For Drug Delivery* Electrochimica Acta. vol. 42, No. 20–22, 1997, pp. 3385–3390.

Mark R. Prausnitz, Georgia Institute of Technology *Transdermal Delivery of Macromolecules: Recent Advances by Modification of Skin's Barrier Properties* ACS Symposium Series 675, Therapeutic Protein and Peptide Formulation and Delivery, Chapter 8, pp. 124–153.

Mark R. Prausnitz, Caroline S. Lee, Cindy H. Liu, Judy C. Pang, Tej–Preet Singh, Robert Langer, James C. Weaver, Massachusets Institute of Technology, Cambridge, MA *Transdermal Transport Efficiency During Skin Electroporation and Iontophoresis* Journal of Controlled Release 38 (1996) pp. 205–217.

* cited by examiner

APPARATUS AND METHOD FOR MANUFACTURING AN INTRACUTANEOUS MICRONEEDLE ARRAY

TECHNICAL FIELD

The present invention relates generally to medical devices and is particularly directed to a fluid dispensing device and a fluid sampling device of the type which penetrates the stratum corneum and epidermis, but not into the dennis of skin. The invention is specifically disclosed as an array of microneedles which painlessly and with minimal trauma to the skin enable fluid transfer either into a body as a dispensing device, or from the body to sample body fluid.

BACKGROUND OF THE INVENTION

Topical delivery of drugs is a very useful method for achieving systemic or localized pharmacological effects. The main challenge in transcutaneous drug delivery is providing sufficient drug penetration across the skin. The skin consists of multiple layers starting with a stratum corneum layer about (for humans) twenty (20) microns in thickness (comprising dead cells), a viable epidermal tissue layer about seventy (70) microns in thickness, and a dermal tissue layer about two (2) mm in thickness.

The thin layer of stratum corneum represents a major barrier for chemical penetration through skin. The stratum corneum is responsible for 50% to 90% of the skin barrier property, depending upon the drug material's water solubility and molecular weight. The epidermis comprises living tissue with a high concentration of water. This layer presents a lesser barrier for drug penetration. The dermis contains a rich capillary network close to the dermal/epidermal junction, and once a drug reaches the dermal depth it diffuses rapidly to deep tissue layers (such as hair follicles, muscles, and internal organs), or systemically via blood circulation.

Current topical drug delivery methods are based upon the use of penetration enhancing methods, which often cause skin irritation, and the use of occlusive patches that hydrate the stratum comeum to reduce its barrier properties. Only small fractions of topically applied drug penetrates through skin, with very poor efficiency.

Convention methods of biological fluid sampling and non-oral drug delivery are normally invasive. That is, the skin is lanced in order to extract blood and measure various components when performing fluid sampling, or a drug delivery procedure is normally performed by injection, which causes pain and requires special medical training. An alternative to drug delivery by injection has been proposed by Henry, McAllister, Allen, and Prausnitz, of Georgia Institute of Technology (in a paper titled "Micromachined Needles for the Transdermal Delivery of Drugs), in which an array of solid microneedles is used to penetrate through the stratum corneum and into the viable epidermal layer, but not to the dermal layer. In this Georgia Tech design, however, the fluid is prone to leakage around the array of microneedles, since the fluid is on the exterior surface of the structure holding the microneedles.

Another alternative to drug delivery by injection is disclosed in U.S. Pat. No. 3,964,482 (by Gerstel), in which an array of either solid or hollow microneedles is used to penetrate through the stratum corneum, into the epidermal layer, but not to the dermal layer. Fluid is to be dispensed either through hollow microneedles, through permeable solid projections, or around non-permeable solid projections that are surrounded by a permeable material or an aperture. A membrane material is used to control the rate of drug release, and the drug transfer mechanism is absorption. The microneedle size is disclosed as having a diameter of 15 gauge through 40 gauge (using standard medical gauge needle dimensions), and a length in the range of 5–100 microns. The permeable material may be filled with a liquid, hydrogel, sol, gel, of the like for transporting a drug through the projections and through the stratum corneum.

Another structure is disclosed in WO 98/00193 (by Altea Technologies, Inc.) in the form of a drug delivery system, or analyte monitoring system, that uses pyramidal-shaped projections that have channels along their outer surfaces. These projections have a length in the range of 30–50 microns, and provide a trans-dermal or trans-mucous delivery system, which can be enhanced with ultrasound.

Another struture, disclosed in WO 97/48440, WO 97/48441, and WO 97/48442 (by ALZA Corp.) is in the form of a device for enhancing transdermal agent delivery or sampling. It employs a plurality of solid metallic microblades and anchor elements, etched from a metal sheet, with a length of 25–400 mm. WO 96/37256 (by Silicon Microdevices, Inc.) disclosed another silicon microblade structure with blade lengths of 10–20 mm. For enhancing transdermal delivery.

Most of the other conventional drug delivery systems involve an invasive needle or plurality of needles. An example of this is U.S. Pat. No. 5,848,991 (by Gross) which uses a hollow needle to penetrate through the epidermis and into the dermis of the subject's skin when the housing containing an expansible/contractible chamber holding a reservoir of fluidic drug is attached to the skin. Another example of this is U.S. Pat. No. 5,250,023 (by Lee) which administers fluidic drugs using a plurality of solid needles that penetrate into the dermis. The Lee drug delivery system ionizes the drug to help transfer the drug into the skin by an electric charge. The needles are disclosed as being within the range of 200 microns through 2,000 microns.

Another example of a needle that penetrates into the dermis is provided in U.S. Pat. No. 5,591,139, WO 99/00155, and U.S. Pat. No. 5,855,801 (by Lin) in which the needle is processed using integrated circuit fabrication techniques. The needles are disclosed as having a length in the range of 1,000 microns through 6,000 microns.

The use of microneedles has great advantages in that intracutaneous drug delivery can be accomplished without pain and without bleeding. As used herein, the term "microneedles" refers to a plurality of elongated structures that are sufficiently long to penetrate through the stratum corneum skin layer and into the epidermal layer, yet are also sufficiently short to not penetrate to the dermal layer. Of course, if the dead cells have been completely or mostly removed from a portion of skin, then a very minute length of microneedle could be used to reach the viable epidennal tissue.

Since microneedle technology shows much promise for drug delivery, it would be a further advantage if a microneedle apparatus could be provided to sample fluids within skin tissue. Furthermore, it would be a further advantage to provide a microneedle array in which the individual microneedles were of a hollow structure so as to allow fluids to pass from an internal chamber through the hollow microneedles and into the skin, and were of sufficient length to ensure that they will reach into the epidermis, entirely through the stratum corneum.

SUMMARY OF THE INVENTION

Accordingly, it is a primary advantage of the present invention to provide a microneedle array in the form of a patch which can perform intracutaneous drug delivery. It is another advantage of the present invention to provide a microneedle array in the form of a patch that can perform interstitial body-fluid testing and/or sampling. It is a further advantage of the present invention to provide a microneedle array as part of a closed-loop system to control drug delivery, based on feedback information that analyzes body fluids, which can achieve real time continuous dosing and monitoring of body activity. It is yet another advantage of the present invention to provide an iontophoretically/microneedle-enhanced transdermal drug delivery system in order to achieve high-rate drug delivery and to achieve sampling of body fluids. It is a yet further advantage of the present invention to provide a method for manufacturing an array of microneedles using microfabrication techniques, including standard semiconductor fabrication techniques. It is still another advantage of the present invention to provide a method of manufacturing an array of microneedles comprising a plastic material by a "self-molding" method, a micromolding method, a microembossing method, or a microinjection method.

Additional advantages and other novel features of the invention will be set forth in part in the description that follows and in part will become apparent to those skilled in the art upon examination of the following or may be learned with the practice of the invention.

To achieve the foregoing and other advantages, and in accordance with one aspect of the present invention, a first embodiment of an improved microneedle array is constructed of silicon and silicon dioxide compounds using MEMS (i.e., Micro-Electro-Mechanical-Systems) technology and standard microfabrication techniques. The microneedle array may be fabricated from a silicon die which can be etched in a microfabrication process to create hollow cylindrical individual microneedles. The resulting array of microneedles can penetrate with a small pressure through the stratum corneum of skin (including skin of animals, reptiles, or other creatures—typically skin of a living organism) to either deliver drugs or to facilitate interstitial fluid sampling through the hollow microneedles. The drug reservoir, and/or the chemical analysis components for sampling body fluid, may be fabricated inside the silicon die, or an additional thick film layer can be bonded or otherwise attached over the silicon substrate to create the reservoir. The delivery of drugs and sampling of fluids can be performed by way of passive diffusion (e.g., time release), instantaneous injection, or iontophoresis. A complete closed-loop system can be manufactured including active elements, such as micro-machined pumps, heaters, and mixers, as well as passive elements such as sensors. A "smart patch" can thereby be fabricated that samples body fluids, performs chemistry to decide on the appropriate drug dosage, and then administers the corresponding amount of drug. Such a system can be made disposable, including one with an on-board power supply.

In a second embodiment, an array of hollow (or solid) microneedles can be constructed of plastic or some other type of molded or cast material. When using plastic, a micro-machining technique is used to fabricate the molds for a plastic microforming process. The molds are detachable and can be re-used. Since this procedure requires only a one-time investment in the mold micro-machining, the resulting plastic microstructure should be much less expensive than the use of microfabrication techniques to construct microneedle arrays, as well as being able to manufacture plastic microneedle arrays much more quickly. It will be understood that such hollow microneedles may also be referred to herein as "hollow elements," or "hollow projections," including in the claims. It will also be understood that such solid microneedles may also be referred to herein as "solid elements," or "solid projections" (or merely "projections"), including in the claims.

Molds used in the second embodiment of the present invention can contain a micropillar array and microhole array (or both), which are fabricated by micro-machining methods. Such micro-machining methods may include micro electrode-discharge machining to make the molds from a variety of metals, including stainless steel, aluminum, copper, iron, tungsten, and their alloys. The molds alternatively can be fabricated by microfabrication techniques, including deep reactive etching to make silicon, silicon dioxide, and silicon carbide molds. Also, LIGA or deep UV processes can be used to make molds and/or electroplated metal molds.

The manufacturing procedures for creating plastic (or other moldable material) arrays of microneedles include: "self-molding," micromolding, microembossing, and microinjection techniques. In the "self-molding" method, a plastic film (such as a polymer) is placed on a micropillar array, the plastic is then heated, and plastic deformation due to gravitational force causes the plastic film to deform and create the microneedle structure. Using this procedure, only a single mold-half is required. When using the micromolding technique, a similar micropillar array is used along with a second mold-half, which is then closed over the plastic film to form the microneedle structure. The micro-embossing method uses a single mold-half that contains an array of micropillars and conical cut-outs (microholes) which is pressed against a flat surface (which essentially acts as the second mold-half) upon which the plastic film is initially placed. In the microinjection method, a melted plastic substance is injected between two micro-machined molds that contain microhole and micropillar arrays.

Of course, instead of molding a plastic material, the microneedle arrays of the present invention could also be constructed of a metallic material by a die casting method using some of the same structures as are used in the molding techniques discussed above. Since metal is somewhat more expensive and more difficult to work with, it is probably not the preferred material except for some very stringent requirements involving unusual chemicals or unusual application or placement circumstances. The use of chemical enhancers, ultrasound, or electric fields may also be used to increase transdermal flow rate when used with the microneedle arrays of the present invention.

In the dispensing of a liquid drug, the present invention can be effectively combined with the application of an electric field between an anode and cathode attached to the skin which causes a low-level electric current. The present invention combines the microneedle array with iontophoresis enhancement, which provides the necessary means for molecules to travel through the thicker dermis into or from the body, thereby increasing the permeability of both the stratum corneum and deeper layers of skin. While the transport improvement through the stratum corneum is mostly due to microneedle piercing, iontophoresis provides higher transport rates in epidermis and dermis.

The present invention can thereby be used with medical devices to dispense drugs by iontophoretic/microneedle enhancement, to sample body fluids (while providing an iontophoretically/microneedle-enhanced body-fluid sensor), and a drug delivery system with fluid sampling feedback using a combination of the other two devices. For example, the body-fluid sensor can be used for a continuous noninvasive measurement of blood glucose level by extracting glucose through the skin by reverse iontophoresis, and measuring its concentration using a bioelectrochemical sensor. The drug delivery portion of this invention uses the microneedle array to provide electrodes that apply an electric potential between the electrodes. One of the electrodes is also filled with an ionized drug, and the charged drug molecules move into the body due to the applied electric potential.

Still other advantages of the present invention will become apparent to those skilled in this art from the following description and drawings wherein there is described and shown a preferred embodiment of this invention in one of the best modes contemplated for carrying out the invention. As will be realized, the invention is capable of other different embodiments, and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification illustrate several aspects of the present invention, and together with the description and claims serve to explain the principles of the invention. In the drawings:

DETAILED DESCRIPTION OF THE PREFERRED EMBODIMENT

Reference will now be made in detail to the present preferred embodiment of the invention, an example of which is illustrated in the accompanying drawings, wherein like numerals indicate the same elements throughout the views.

Figure 1:
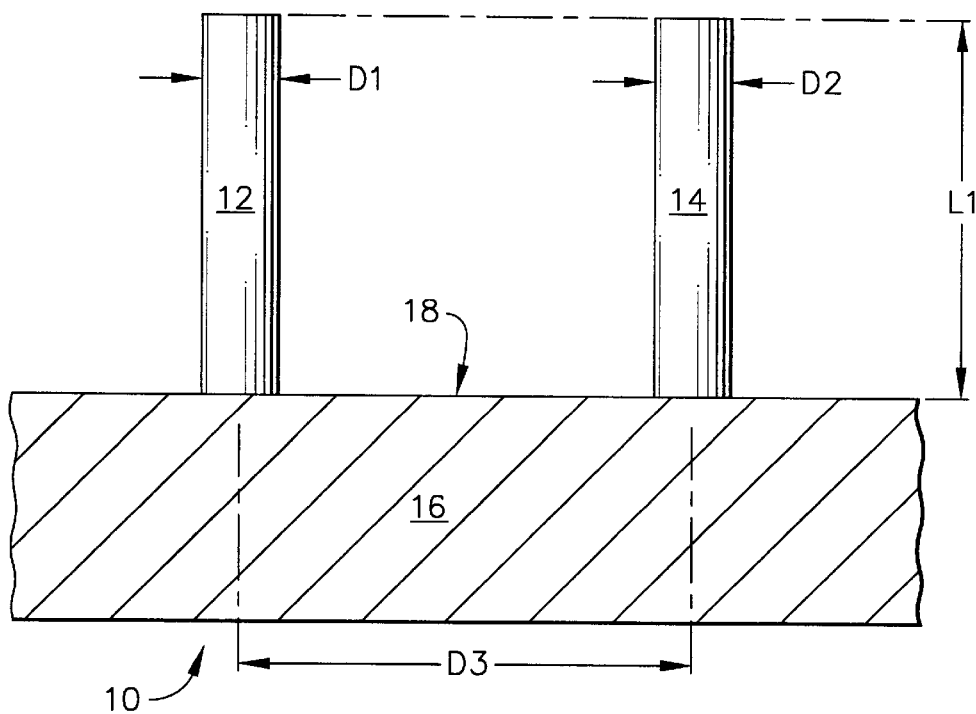
FIG. 1 is an elevational view in partial cross-section of a bottom mold provided at the initial step of a "self-molding" method of manufacturing an array of plastic microneedles, as constructed according to the principles of the present invention.

Referring now to the drawings, FIG. 1 shows a mold generally designated by the reference numeral 10 that comprises a plurality of micropillars, including micropillars 12 and 14, that are mounted to a base 16 having a planar upper surface 18. Micropillar 12 preferably is cylindrical in shape, and has an outer diameter designated "D1," whereas micropillar 14 (which also preferably is cylindrical in shape) has a diameter designated "D2." The centerlines of micropillars 12 and 14 are separated by a distance "D3," and the vertical height of micropillars 12 and 14 is designated by the letter "L1."

In a preferred configuration, the diameters D1 and D2 are in the range of 1–49 microns, more preferably about ten (10) microns (i.e., 10 microns=10 micrometers), the height L1 in the range of 50–200 microns, whereas the separation distance D3 is in the range of 50–1000 microns, more preferably from 50–200 microns.

Microelectrode-discharge machining can be used to fabricate the mold 10 from metals, such as stainless steel, aluminum, copper, iron, tungsten, or other metal alloys. Mold 10 could also be fabricated from silicon or silicon carbide using integrated circuit processing, or photolithographic processing.

Figure 2:
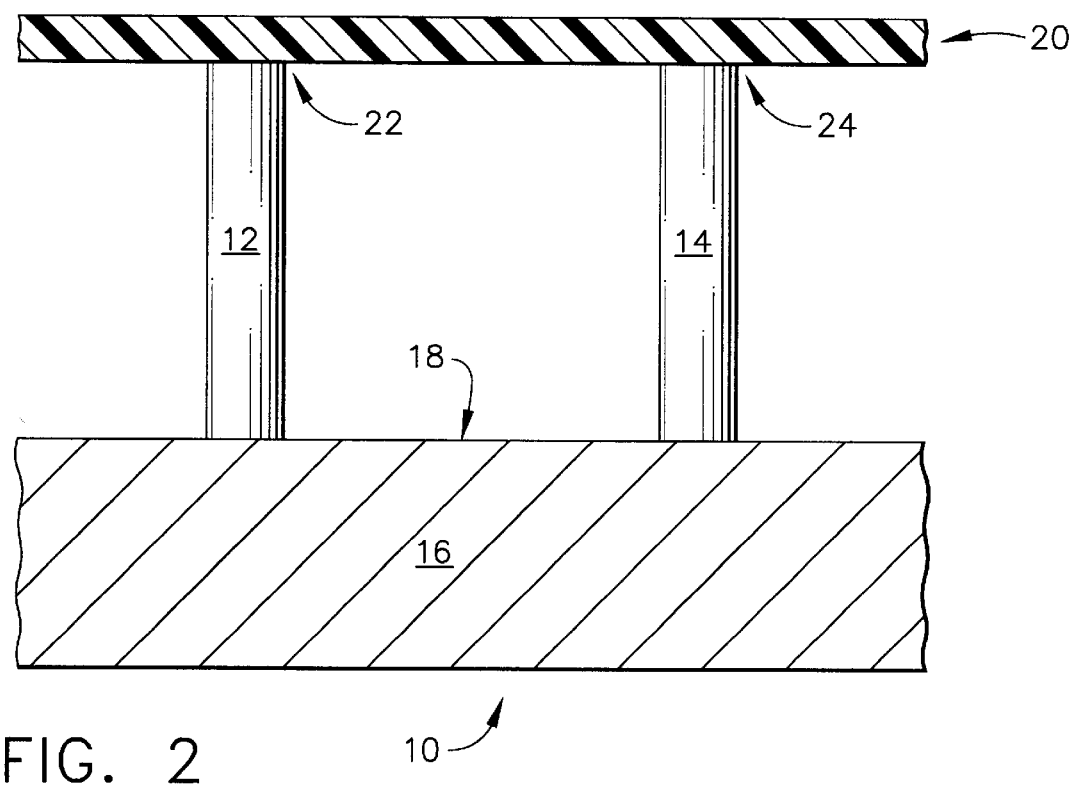
FIG. 2 is an elevational view in partial cross-section of the mold of FIG. 1 in a second step of the self-molding procedure.

FIG. 2 depicts the mold 10 and a thin layer of plastic, such as a polymer film, designated by the reference numeral 20, which is placed on the micropillars 12 and 14, thereby making contact at the reference numerals 22 and 24, respectively. Once the polymer film is placed on the micropillars, the polymer is heated to just above the melting temperature of the plastic material. Micropillars 12 and 14 are also heated to a certain extent, but are held just below the melting temperature of the plastic material. This establishes a temperature gradient within the plastic film, after which the plastic film is subjected to natural gravitational forces, or placed in a centrifuge. Furthermore, an air-pressure gradient also can be established across the deforming plastic film, by applying pressure from above, or by applying a vacuum from below the film level. The overall effect on the plastic film is that it will undergo a "self-molding" operation, by way of the gravitational force or centrifugal force, and the air-pressure gradient can be used to accelerate the self-molding process.

Figure 3:
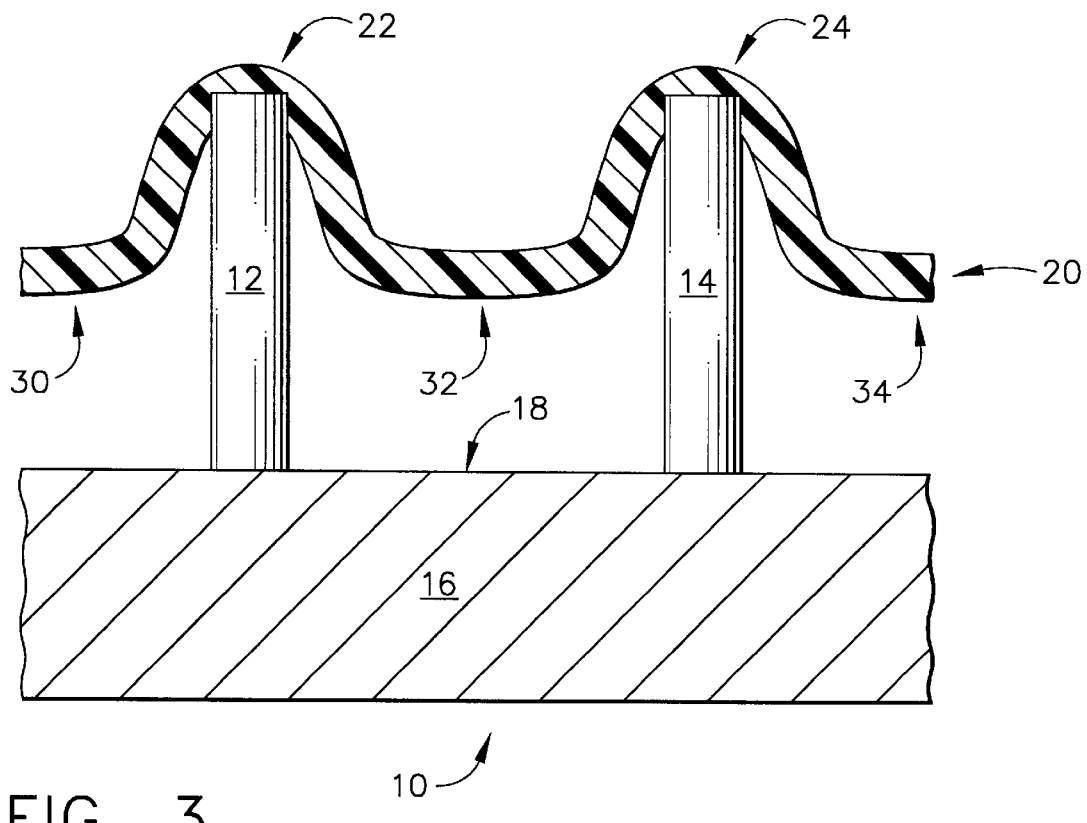
FIG. 3 is an elevational view in partial cross-section of the mold of FIG. 1 in a third step of the self-molding procedure.

FIG. 3 depicts the mold 10 at a further step in the processing of the plastic film, showing the result of the temperature gradient. This result is that the areas contacting the micropillars (at the reference numerals 22 and 24) will have a smaller deformation as compared to the remaining portions of the plastic film 20 that are between the pillars 12 and 14. Therefore, the portions 30, 32, and 34 of the plastic material will undergo greater deformation, as viewed on FIG. 3.

Figure 4:
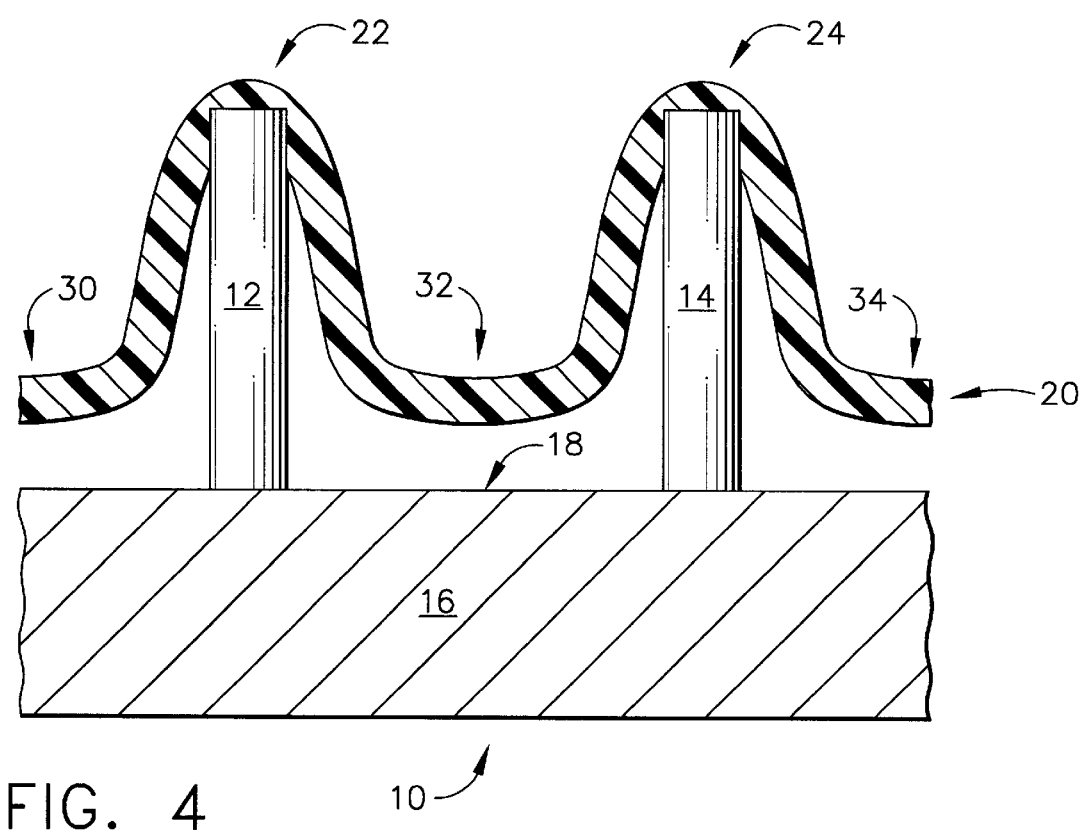
FIG. 4 is an elevational view in partial cross-section of the mold of FIG. 1 in a fourth step of the self-molding procedure.

FIG. 4 depicts the mold 10 at yet a later step in the self-molding process, showing the initial stage in which the mold (including micropillars 12 and 14) is heated above the melting temperature of the plastic material 20. During this latter stage of the self-molding process, the plastic material will continue to melt and to be removed from the tops of the pillars 12 and 14. As viewed in FIG. 4, the remaining portions not in contact with micropillars 12 and 14 will continue to deform downward (as viewed on FIG. 4) at the reference numerals 30, 32, and 34.

Figure 5:
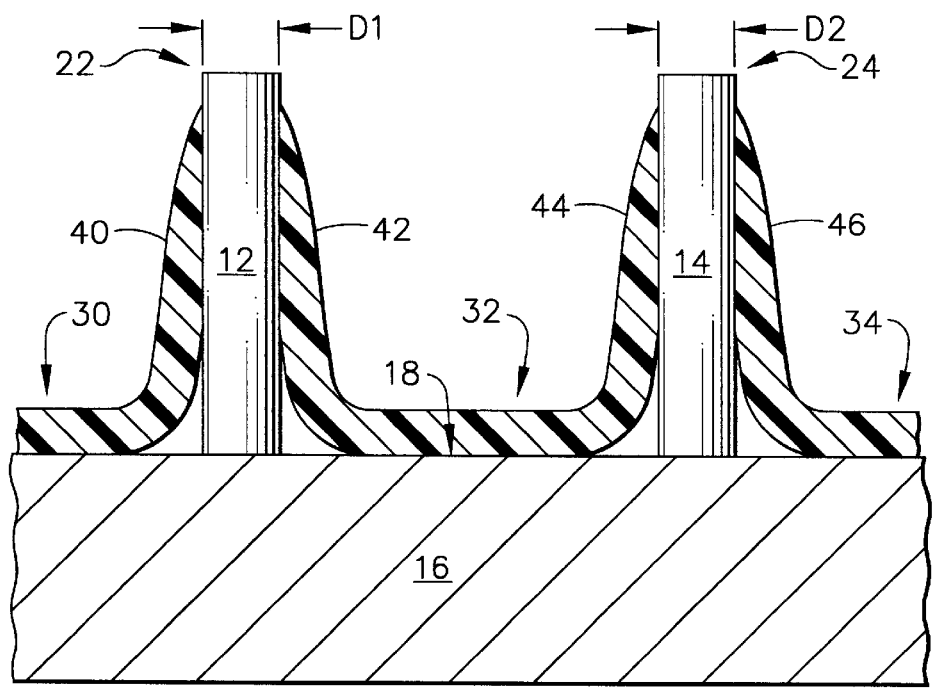
FIG. 5 is an elevational view in partial cross-section of the mold of FIG. 1 in a fifth step of the self-molding procedure.

FIG. 5 depicts the mold 10 at the final stage of self-molding, which illustrates the fact that the plastic material has completely melted down and away from the tops 22 and 24 of the micropillars 12 and 14. At this point the mold and the plastic material are both cooled down, thereby forming the final shape that will become the microneedles. This final shape includes an outer wall 40 and 42 for the microneedle being formed by micropillar 12, and an outer wall at 44 and 46 for the microneedle being formed at the micropillar 14.

Figure 6:
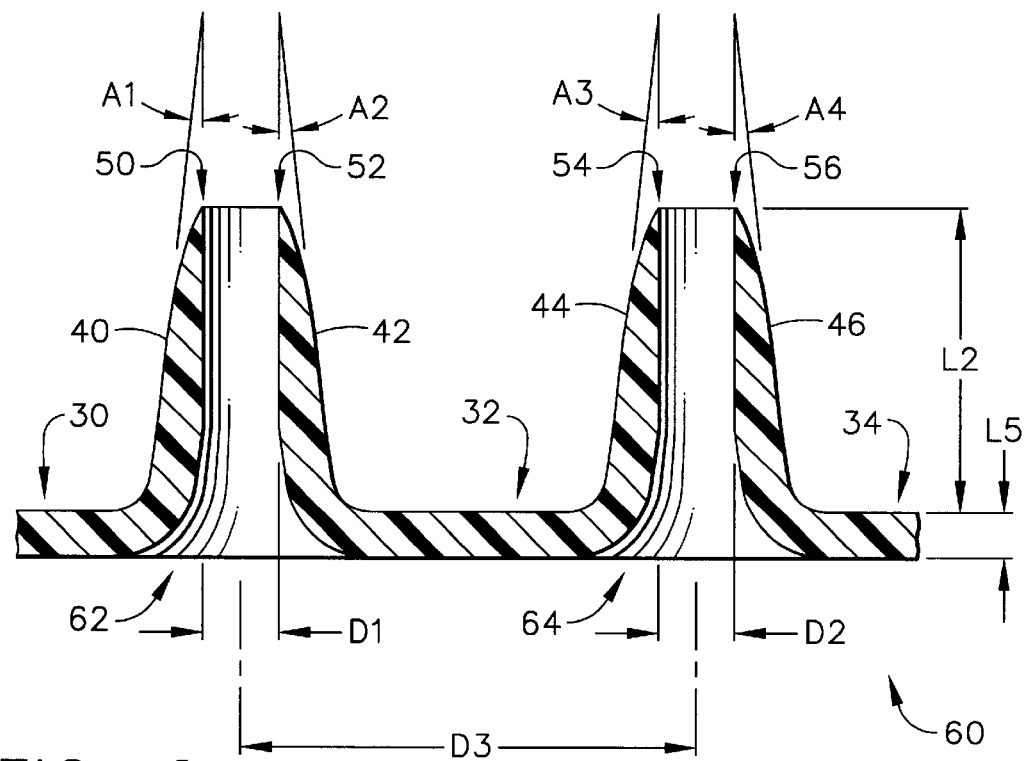
FIG. 6 is an elevational view in cross-section of an array of hollow microneedles constructed according to the self-molding procedure depicted in FIGS. 1–5.

FIG. 6 illustrates the cross-sectional shape of the microneedle array, s generally designated by the reference numeral 60, after it has been detached from the mold 10. The left hand microneedle 62 has a relatively sharp upper edge, which appears as points 50 and 52. Its outer wall is illustrated at 40 and 42, which are sloped with respect to the vertical, as designated by the angles "A1" and "A2." The right-hand side microneedle 64 exhibits a similar sharp top edge, as indicated by the points 54 and 56, and also exhibits a sloped outer wall at 44 and 46. The angle of this outer wall is indicated at the angles "A3" and "A4." The preferred value of angles A1–A4 is in the range of zero (0) to forty-five (45) degrees.

The inner diameter of the left-hand microneedle 62 is indicated by the distance "D1," and the inner diameter of the right-hand microneedle 64 is indicated by the distance "D2." These distances D1 and D2 are substantially the same distance as the diameter of micropillars 12 and 14, as indicated in FIG. 1. Furthermore, the distance D3 between the centerlines of the microneedles on FIG. 6 is essentially the same as the distance D3 between the micropillars on FIG. 1. The length "L2" of the microneedles on FIG. 6 is somewhat less than the length L1 on FIG. 1, although this length L2 could theoretically be a maximum distance of L1.

It will be understood that the plastic material (also referred to herein as the "polymer film") may consist of any type of permanently deformable material that is capable of undergoing a gradual deformation as its melting point is reached or slightly exceeded. This "plastic material" could even be some type of metallic substance in a situation where the metallic material would deform at a low enough temperature so as to not harm the mold itself. The preferred material is a polyamide such as nylon, although many other types of polymer material certainly could be used to advantage. Other potential materials include: polyesters, vinyl, polysterene, polycarbonate, and acrylonitrilebutadisterene (ABS). Of course, one important criterion is that the material which makes up the microneedles does not chemically react with skin, or with the fluidic substance that is being transported through the hollow interiors of the microneedle array.

Figure 7:
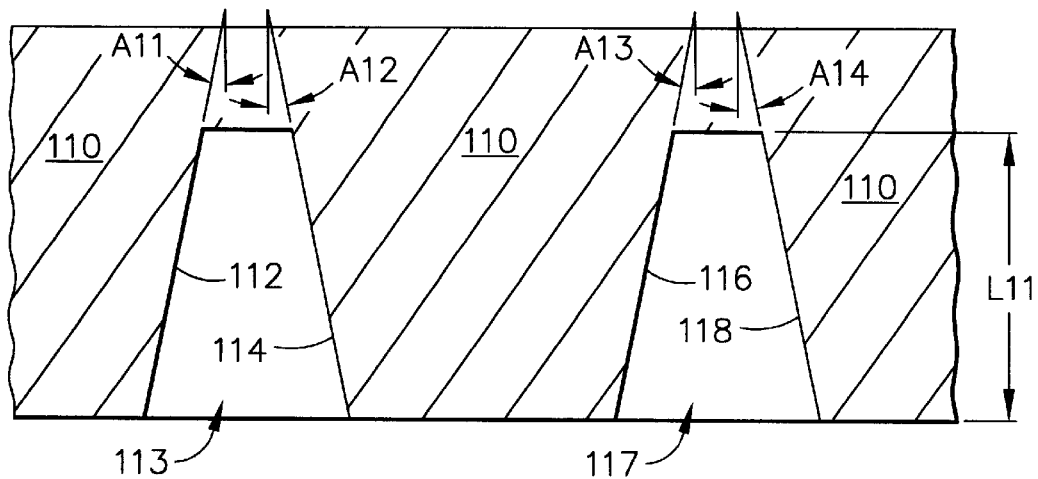
FIG. 7 is a cross-sectional view of a top mold-half used in a micromolding procedure, according to the principles of the present invention.

FIG. 7 depicts a top mold-half, generally designated by the reference numeral 110, of a second embodiment of the present invention in which the manufacturing method for creating an array of hollow microneedles is performed by a micromolding procedure. The top mold-half 110 includes two "microholes" that have sloped side walls, designated by the reference numerals 112 and 114 for the left-hand microhole 113, and by the reference numerals 116 and 118 for the right-hand microhole 117. The microholes 113 and 117 have a vertical (in FIG. 7) dimension referred to herein as a distance "L11". Microholes 113 and 117 correspond to a pair of micropillars 122 and 124 that are part of a bottom mold-half, generally designated by the reference number 120, and illustrated in FIG. 8.

Referring back to FIG. 7, the sloped side walls of the microhole 113 are depicted by the angles "A11" and "A12," with respect to the vertical. The side walls of microhole 117 are also sloped with respect to the vertical, as illustrated by the angles "A13" and "A14" on FIG. 7. Since microhole 113 preferably is in a conical overall shape, the angle A11 will be equal to the angle A12; similarly for microhole 117, the angle A13 will be equal to the angle A14. It is preferred that all microholes in the top mold-half 110 exhibit the same angle with respect to the vertical, which means that angles A11 and A13 are also equal to one another. A preferred value for angles A11–A14 is in the range of zero (0) through forty-five (45) degrees. The larger the angle from the vertical, the greater the trauma to the skin tissue when a microneedle is pressed against the skin. On FIG. 7, the illustrated angle A11 is approximately twelve (12) degrees.

Figure 8:
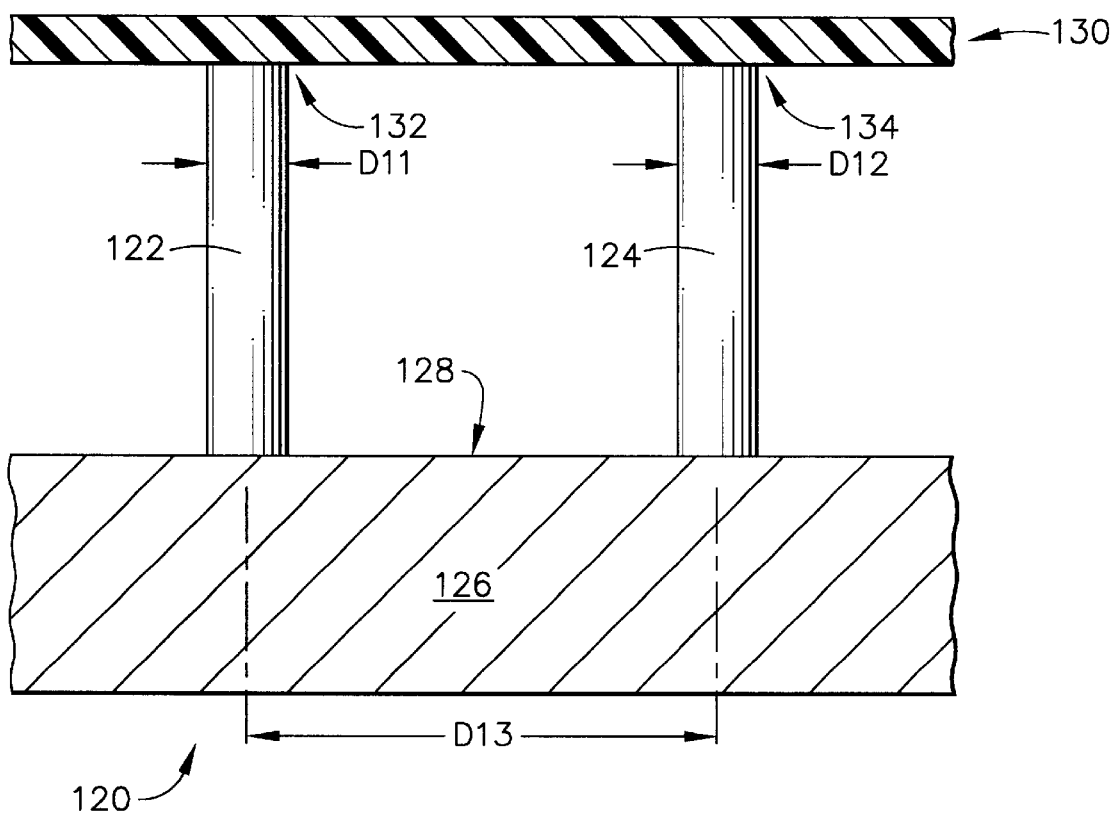
FIG. 8 is an elevational view of the bottom half of the mold that mates to the top mold-half of FIG. 7, and which is used to form plastic microneedles according to the micromolding procedure.

Referring now to FIG. 8, the bottom mold-half 120 includes a base 126 having a substantially planar top surface 128, upon which the two micropillars 122 and 124 are mounted. These micropillars are preferably cylindrical in shape, and have a diameter of D11 and D12, respectively. The distance between the centerlines of these micropillars is designated as D13. Diameters D11 and D12 preferably are in the range 1–49 microns, more preferably about 10 microns. The distance "D13" represents the separation distance between the center lines of micropillars 122 and 124, which preferably is in the range 50–1000 microns, more preferably about 200 microns.

The two mold-halves 110 and 120 can be fabricated from metals using microelectrode-discharge machining techniques. Alternatively, the molds could be fabricated from silicon or silicon carbide using integrated circuit processing or lithographic processing.

Figure 9:
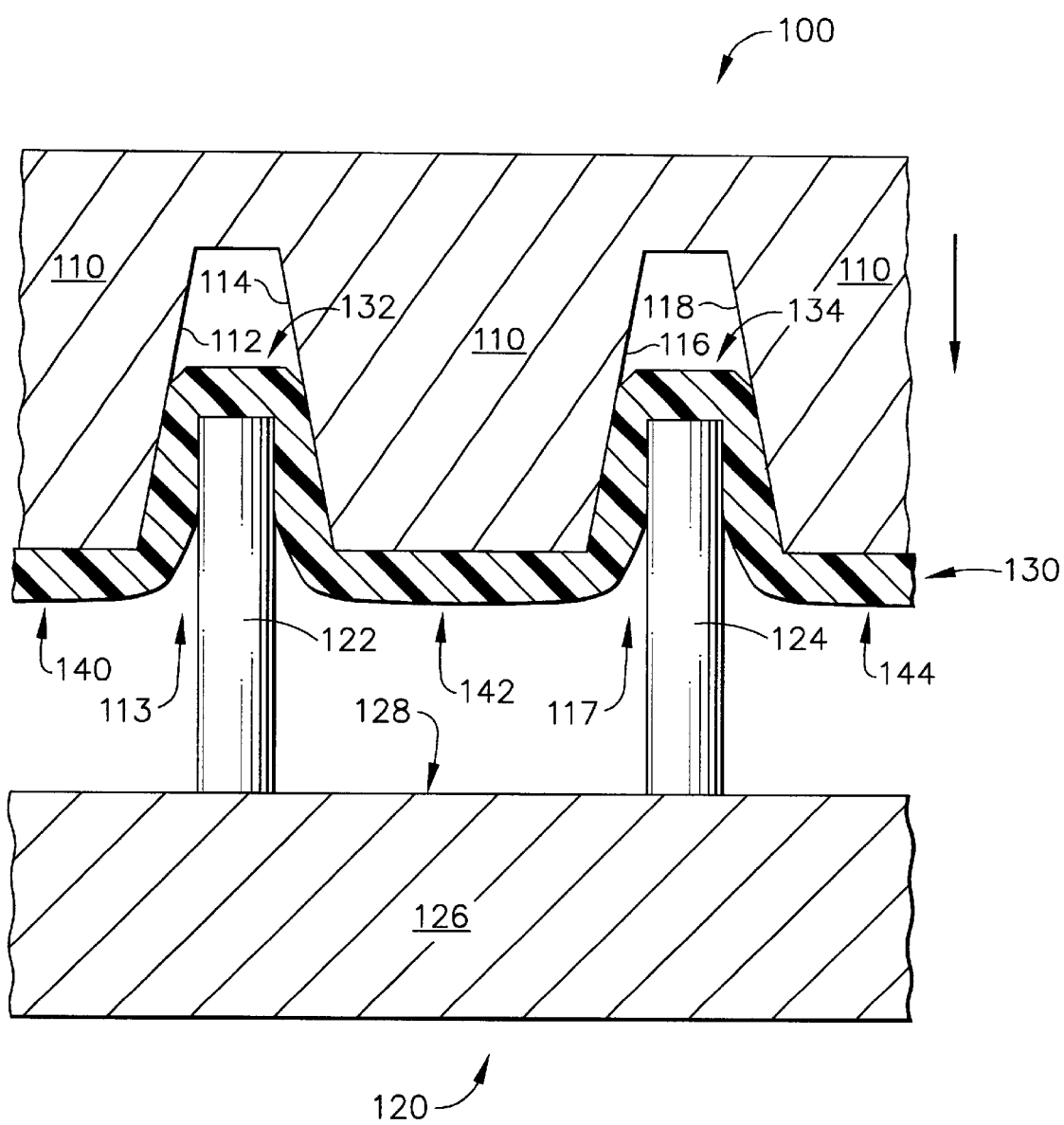
FIG. 9 is an elevational view in partial cross-section of one of the method steps in the micromolding procedure using the mold halves of FIGS. 7 and 8.

On FIG. 8, a thin plastic film, generally designated by the reference numeral 130, is placed on top of the micropillars and heated above the glass transition temperature of the plastic material while the plastic material 130 rests upon the tops of the pillars at 132 and 134, thereby causing the plastic material to become sufficient pliable or "soft" for purposes of permanently deforming the material's shape. Preferably, the temperature of the plastic material will not be raised above its melting temperature, although it would not inhibit the method of the present invention for the plastic material to become molten just before the next step of the procedure. In FIG. 9, the top mold-half 110 is pressed downward and begins to deform the plastic film 130. While a portion of the plastic material 130 temporarily resides above the micropillars at 132 and 134, a larger amount of the plastic material is pressed downward directly by the mold top-half 110 at 140, 142, and 144. As can be seen in FIG. 9, the two mold halves 110 and 120 are aligned so that the microholes 113 and 117 correspond axially to the micropillars 122 and 124, respectively. The two mold halves now begin to operate as a single mold assembly, generally designated by the reference numeral 100.

Figure 10:
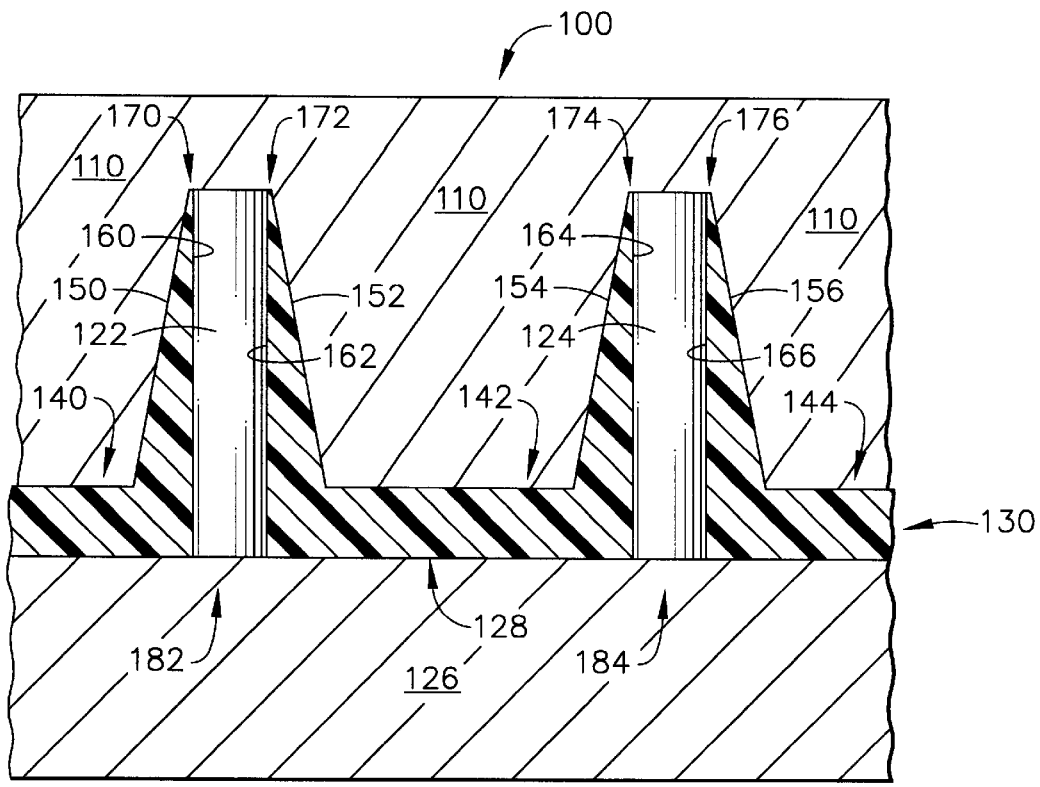
FIG. 10 is an elevational view in partial cross-section of the mold of FIG. 9 depicting the next step in the micromolding procedure.

In FIG. 10, the two mold halves 110 and 120 have completely closed, thereby squeezing all of the plastic material 130 away from the tops of the micropillars 122 and 124. At this point, the plastic microneedles are formed, and the mold and the plastic material are both cooled down.

The wall 112 and 114 of the first microhole 113 causes a side outer wall to be formed out of the plastic material at 150 and 152. The corresponding inner wall of the microneedle 182 is depicted at 160 and 162, which is caused by the shape of the micropillar 122. Since the outer wall is sloped, it will converge with the inner wall 160 and 162, near the top points at 170 and 172. A similar outer wall 154 and 156 is formed by the inner wall 116 and 118 of microhole 117. The inner wall of the microneedle 184 is depicted at 164 and 166, and these inner and outer walls converge near points 174 and 176.

Figure 11:
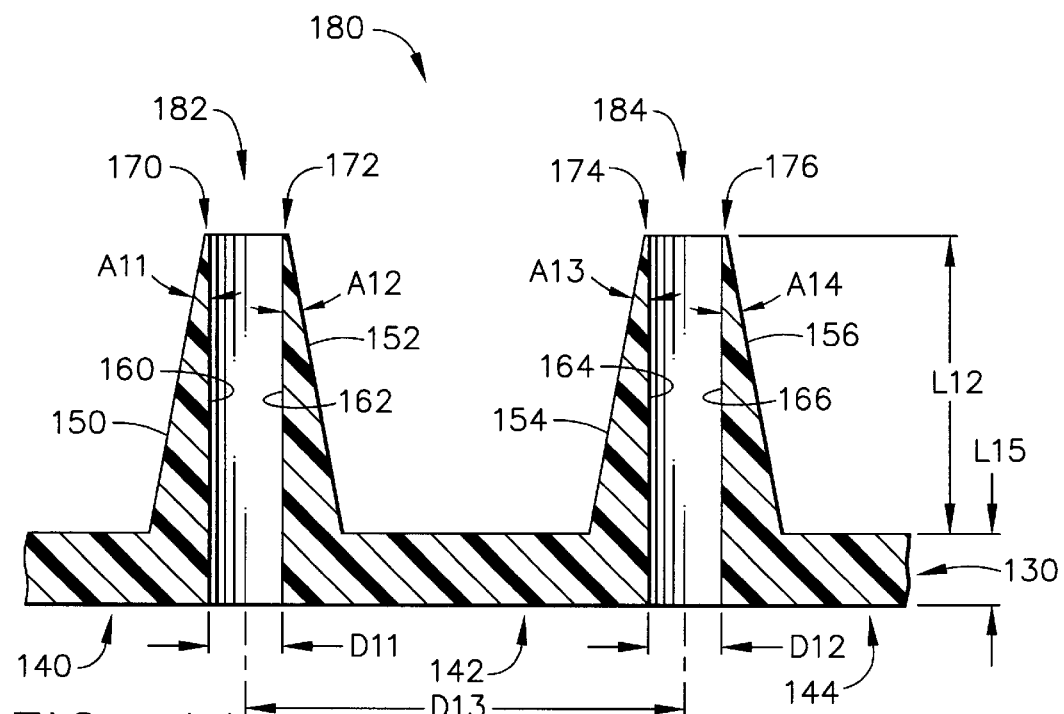
FIG. 11 is a cross-sectional view of an array of plastic microneedles constructed according to the micromolding procedure depicted in FIGS. 7–10.

FIG. 11 illustrates the microneedle array, generally designated by the reference numeral 180, after the mold is removed from the plastic material 130. A lower relatively planar base remains, as illustrated at 140, 142, and 144. On FIG. 11, two different microneedles are formed at 182 and 184. The angles formed by the walls are as follows: angle A11 by walls 150 and 160, angle A12 by walls 162 and 152, angle A13 by walls 154 and 164, and angle A14 by walls 166 and 156. The points at the top if the microneedles (designated at 170, 172, 174, and 176) are fairly sharp, and this sharpness can be adjusted by the shape of the mold with respect to the microholes and micropillar orientations.

The inner diameter of .croneedle 182 is designated by the distance D11, and the inner diameter of the microneedle 184 is designated by the distance D12. The distance between the centerlines of these microneedles is designated as D13. These distances correspond to those illustrated on FIG. 8.

It is preferred that all of the angles A11–A14 are equal to one another, and that the angles fall within the range of zero (0) to forty-five (45) degrees. The preferred angle really depends upon the strength of the material being used to construct the mnicroneedles, in which a greater angle (e.g., angle A11) provides greater strength. However, this angular increase also causes greater trauma to the skin.

Microneedle array 180 also includes a relatively flat base structure, as indicated at the reference numerals 140, 142, and 144. This base structure has a vertical thickness as designated by the dimension L15 (see FIG. 11). The microneedle height is designated by the dimension L12 on FIG. 11. The height must be sufficient to penetrate the skin through the stratum comeum and into the epidermis, and a preferred dimension for height L12 is in the range of 50–200 microns (although, certainly microneedles shorter than 50 microns in length could be constructed in this manner—for use with skin cosmetics, for example). The thickness L15 can be of any size, however, the important criterion is that it be thick enough to be mechanically sound so as to retain the microneedle structure as it is used to penetrate the skin.

Figure 12:
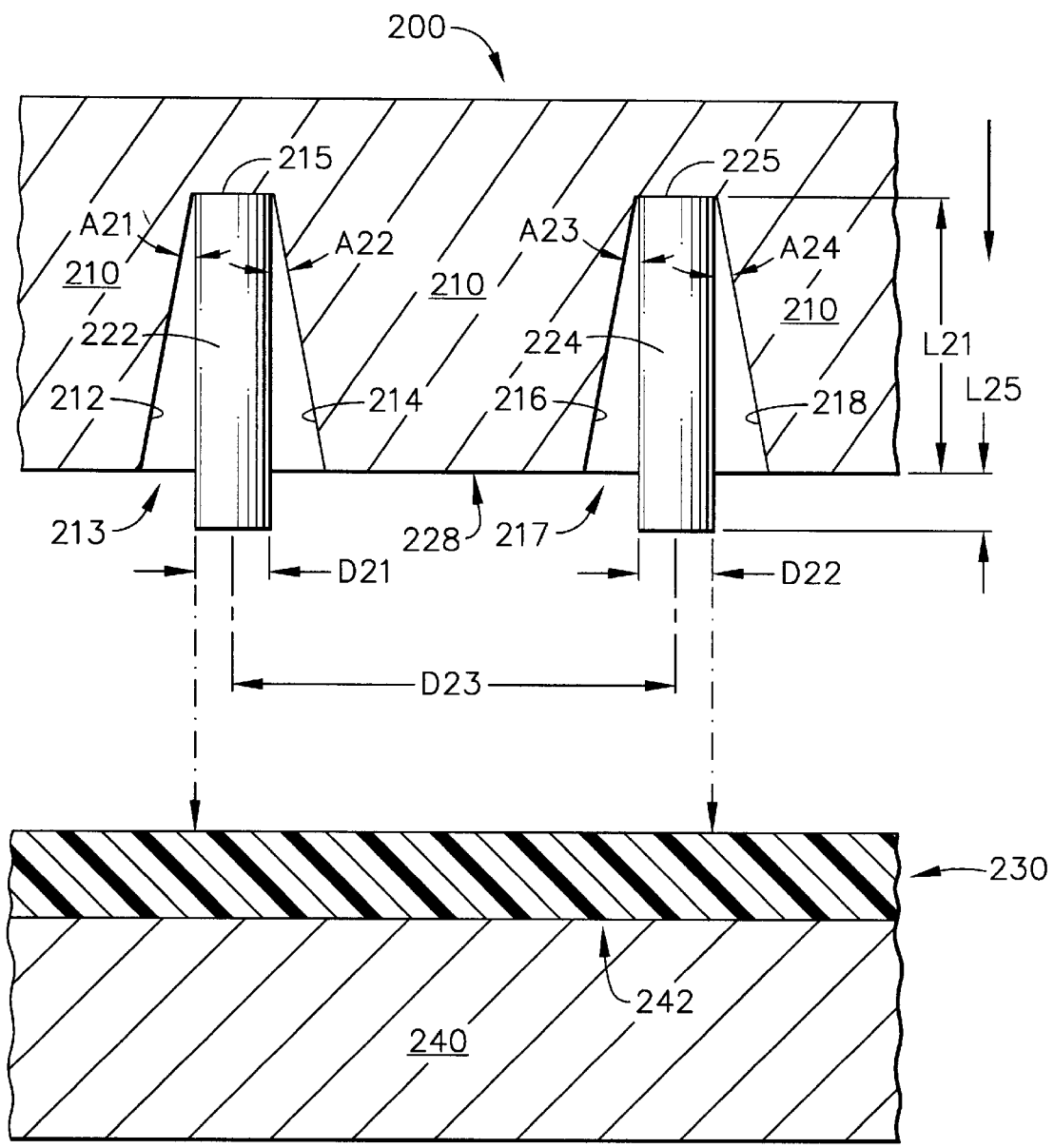
FIG. 12 is an elevational view in partial cross-section of a top mold-half and a bottom planar surface used in creating an array of molded, plastic microneedles by a microembossing procedure, as constructed according to the principles of the present invention.

Referring now to FIG. 12, a top mold-half 210 is combined with a planar bottom mold-half 240 to create an entire mold, generally designated by the reference numeral 200. The top mold-half 210 contains an array of microholes with micropillars at the center of each of the microholes. For example, a microhole 213, having its conical wall at 212 and 214, is preferably concentric with a micropillar 222, and a microhole 217, having its conical wall at 216 and 218, is preferably concentric with a micropillar 224.

The fabrication method used in conjunction with the mold 200 is referred to herein as "microembossing" for the reason that the bottom mold-half 240 is simply a flat or planar surface. This greatly simplifies the construction of this particular mold. A thin plastic film at 230 is placed upon the top surface 242 of this bottom mold-half 240. In the later steps, it will be seen that the plastic material 230 is heated while the top mold-half 210 is pressed down against the bottom mold-half 240.

Microhole 213 and micropillar 222 have an angular relationship as illustrated by the angles "A21" and "A22." A similar angular relationship exists for microhole 217 and micropillar 224, as illustrated by the angles "A23" and "A24." These angles A21–A24 will preferably be in the range of zero (0) to forty-five (45) degrees from the vertical. As noted hereinabove, the greater the angle, the greater the transport rate, however, also the greater trauma to the skin tissue when used.

Micropillar 222 preferably has a cylindrical shape with an outer diameter designated at "D21," and micropillar 224 similarly has a preferred cylindrical shape having a diameter "D22." Diameters D21 and D22 preferably are in the range 1–49 microns, more preferably about 10 microns. The distance "D23" represents the separation distance between the center lines of micropillars 222 and 224, which preferably is in the range 50–1000 microns, more preferably about 200 microns.

The length of the micropillars from the bottom surface 228 of the top mold-half 210 to the closed end of the microholes at 215 and 225, respectively, is designated as the length "L21." The micropillars 222 and 224 are somewhat longer than this length L21, since they are to mate against the upper surface 242 of the bottom mold-half 240, and therefore are longer by a distance designated as "L25." In this manner, the microneedles will be hollow throughout their entire length. The combined length of dimensions L21 and L25 preferably will be approximately 150 microns.

The molds 210 and 240 will preferably be made from a metal, in which microelectrode-discharge machining can be used to fabricate such metallic molds. Alternatively, the molds could be fabricated from silicon or silicon carbide, for example, using integrated circuit processing or lithographic processing.

Figure 13:
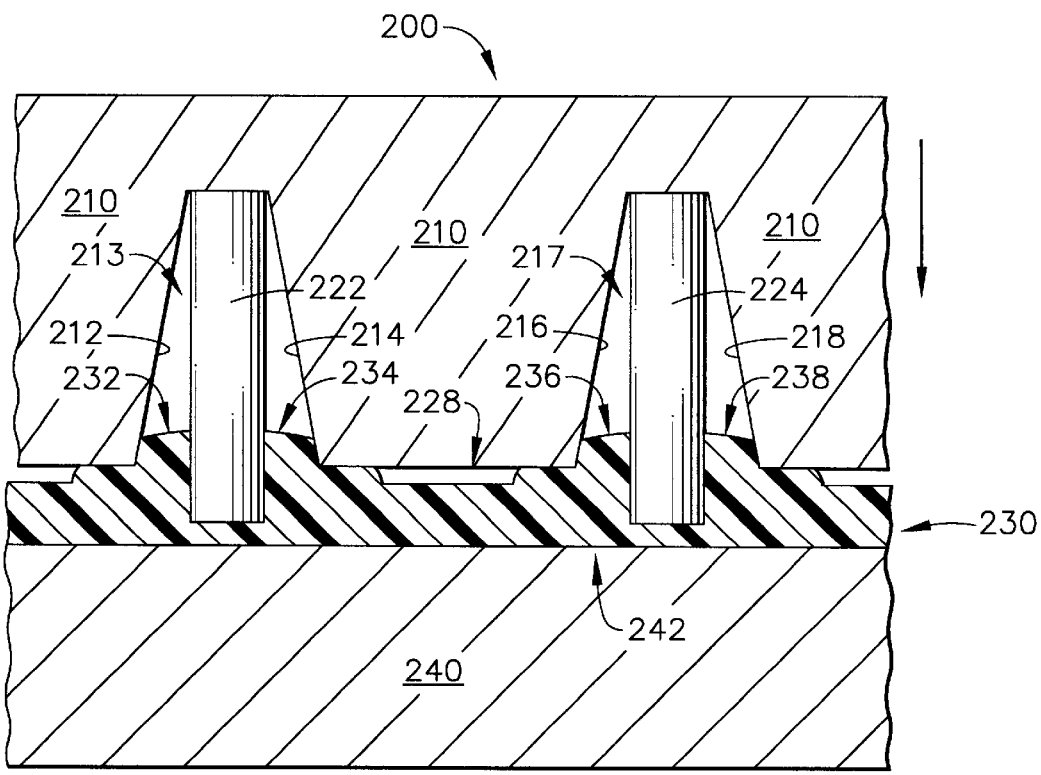
FIG. 13 is an elevational view in partial cross-section of the mold of FIG. 12 in a subsequent process step of the microembossing method.

Referring now to FIG. 13, after the plastic material is heated above its glass transition temperature, thereby causing the plastic material to become sufficient pliable or "soft" for purposes of permanently deforming the material's shape. Preferably, the temperature of the plastic material will not be raised above its melting temperature, although it would not inhibit the method of the present invention for the plastic material to become molten just before the top mold 210 begins to be pressed down against the plastic material 230. This top mold movement begins to deform that plastic material 230 such that it begins to fill the microholes, as illustrated at 232 and 234 (for microhole 213) and at 236 and 238 (for microhole 217).

Figure 14:
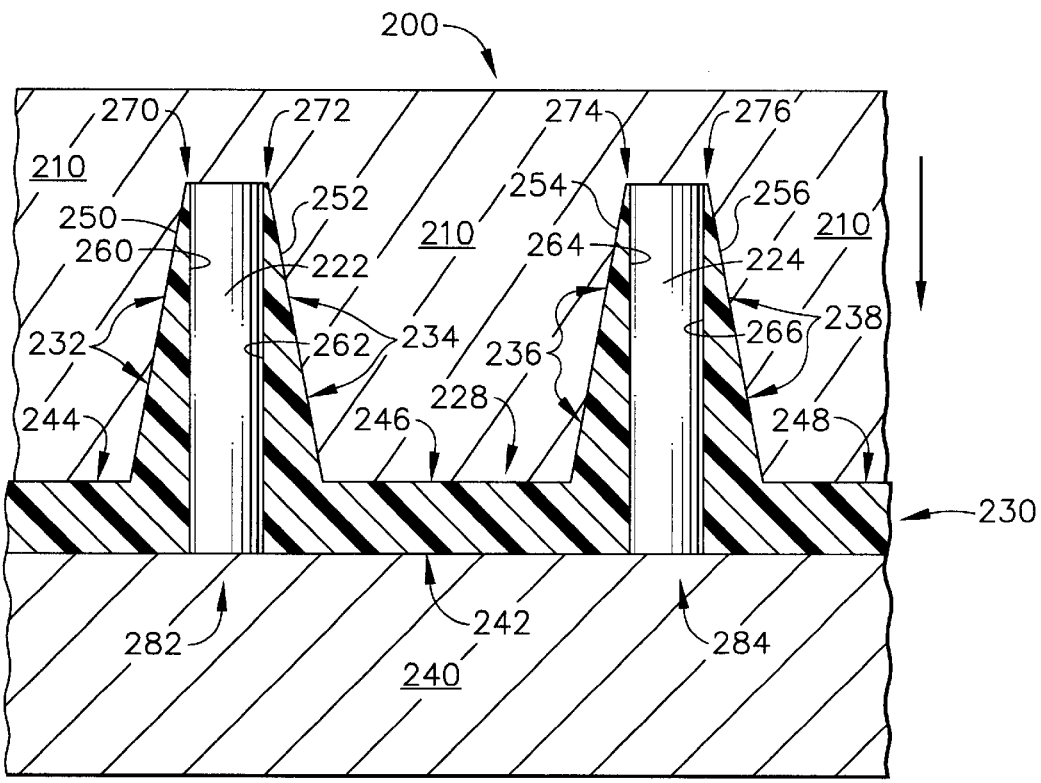
FIG. 14 is an elevational view in partial cross-section of the mold if FIG. 12 showing a later step in the microembossing procedure.

In FIG. 14, the top mold-half 210 has now been completely closed against the bottom planar mold-half 240, and the plastic material 230 has now completely filled the microholes, as illustrated at 232, 234, 236, and 238. The shape of the plastic material now has a conical outer wall at 250 and 252, and a corresponding cylindrical inner wall at 260 and 262, for the left-hand microneedle 282 on FIG. 14. Correspondingly for the right-hand microneedle 284, the plastic material shape has an outer conical wall at 254 and 256, as well as a cylindrical inner wall at 264 and 266. The conical outer walls and the cylindrical inner walls converge at the top points 270 and 272, and 274 and 276. The bottom surface 228 of the top mold-half 210 causes a base to be formed in the plastic material 230 at the locations indicated by the reference numerals 244, 246, and 248. Once this shape has been formed, the mold and the plastic material are cooled down, and then the molds are separated so that the plastic microneedle array is detached to form the shape as illustrated in FIG. 15.

Figure 15:
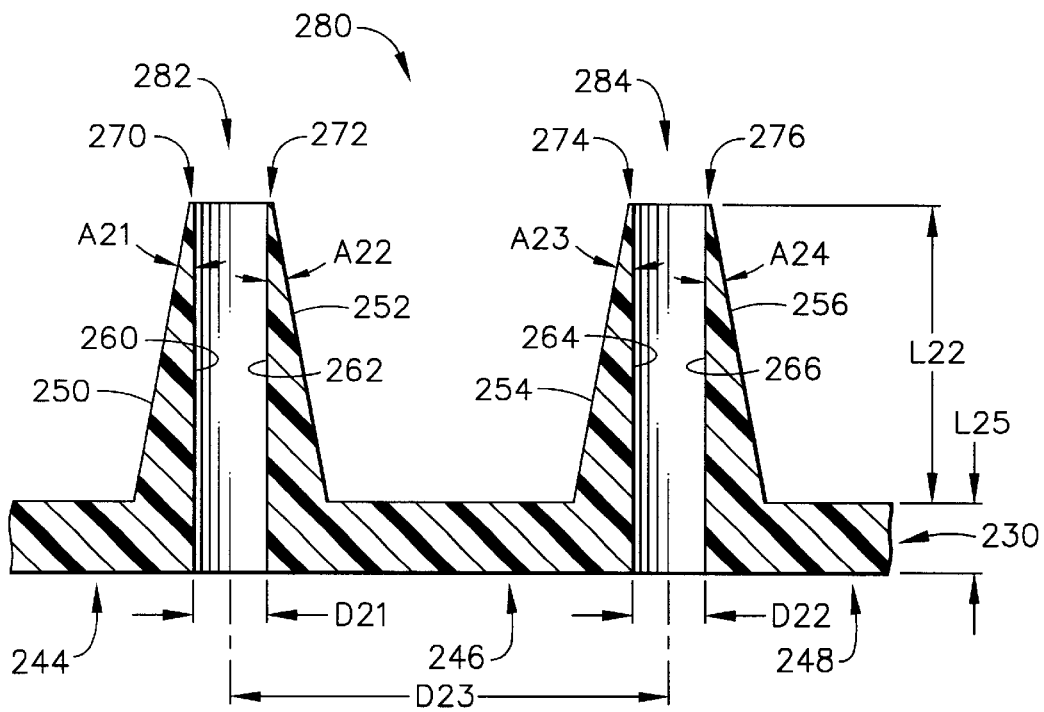
FIG. 15 is a cross-sectional view of a microneedle array of hollow microneedles constructed by the mold of FIGS. 12–14.

In FIG. 15, a microneedle array 280 has been formed out of the plastic material 230, which as viewed on FIG. 15 depicts two microneedles 282 and 284. The left-hand microneedle 282 comprises an outer conical wall as viewed at 250 and 252, and a hollow interior cylindrical wall at 260 and 262. These walls converge at the top points (as viewed on this Figure) at 270 and 272, and the convergence angle is given as "A21" and "A22." The right-hand microneedle 284 comprises an outer conical wall 254 and 256 and a hollow interior cylindrical wall 262 and 264. These walls converge at the top points (on this Figure) at 274 and 276, and the convergence angle is given as "A23" and "A24." Angles A21–A24 are preferably in the range of zero (0) to forty-five (45) degrees.

Microneedle array 280 also includes a relatively flat base structure, as indicated at the reference numerals 244, 246, and 248. This base structure has a vertical thickness as designated by the dimension L25. The microneedle height is designated by the dimension L22. The height must be sufficient to penetrate the skin through the stratum corneum and into the epidennis, and has a preferred dimension in the range of 50–200 microns (although, as noted above, much shorter microneedles could be constructed in this manner). The thickness L25 can be of any size, however, the important criterion is that it be thick enough to be mechanically sound so as to retain the microneedle structure as it is used to penetrate the skin.

The inside diameter of the hollow microneedles is illustrated as D21 and D22, which correspond to the diameters of a cylindrical hollow opening. The distance D23 represents the separation distance between the centerlines of the two microneedles 282 and 284, in this array 280.

Figure 15A:
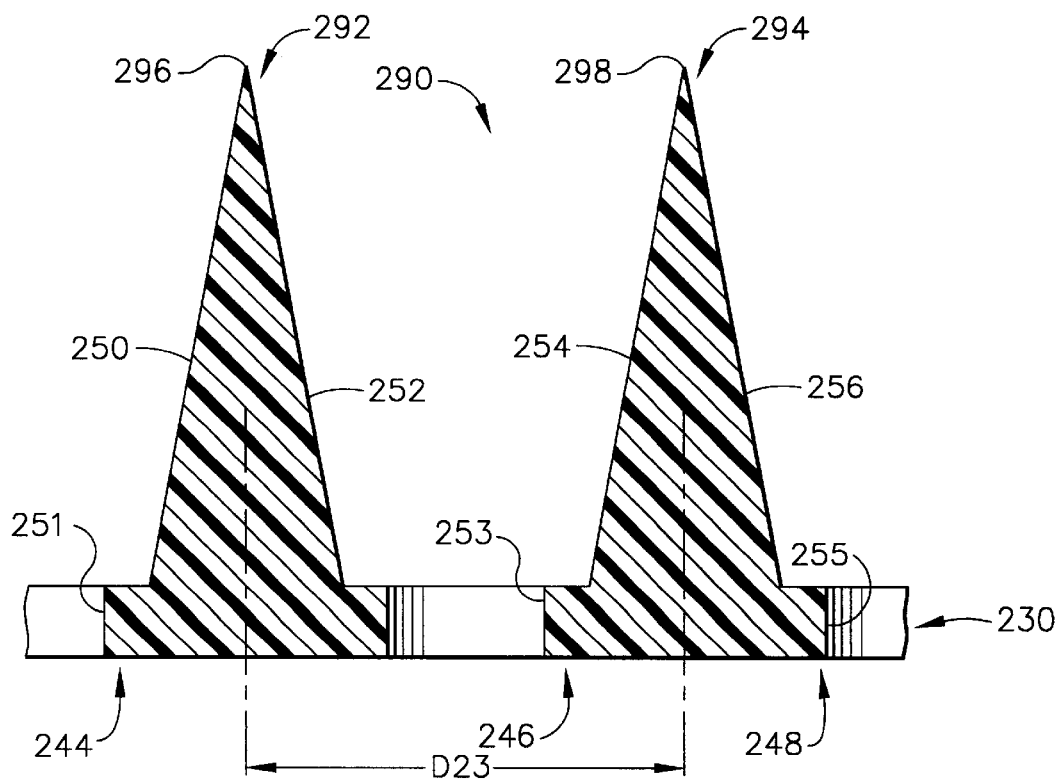
FIG. 15A is a cross-sectional view of an array of microneedles which are not hollow, and are constructed according to the mold of FIGS. 12–14 without the micropillars.

FIG. 15A represents an alternative embodiment in which a microneedle array 290 comprises "solid" microneedles 292 and 294, rather than hollow microneedles as seen at 282 and 284 on FIG. 15. These solid microneedles 292 and 294 are formed by a similar mold as viewed on FIG. 12, but with the micropillars 222 and 224 removed from this mold, and a change in shape of the microholes 213 and 217. This simple change allows the solid microneedles to be formed within conical microholes (not shown on FIG. 12), and produces a pointed conical shape, as exhibited by the outer conical wall 250 and 252 for microneedle 292, with a top pointed surface at 296. Similarly, the microneedle 294 has a conical outer wall 254 and 256, with a similar top pointed surface at 298. The other dimensions and features of the solid microneedle array 290 can be exactly the same as those features of the hollow microneedle array 280 of FIG. 15, or the dimensions may be different since this is for a different application.

The holes 251, 253, 255, can be fabricated during the microstamping or microembossing procedure via inclusion of appropriate micropillars located adjacent to the microholes 213 and 217 in FIG 12.

Figure 16:
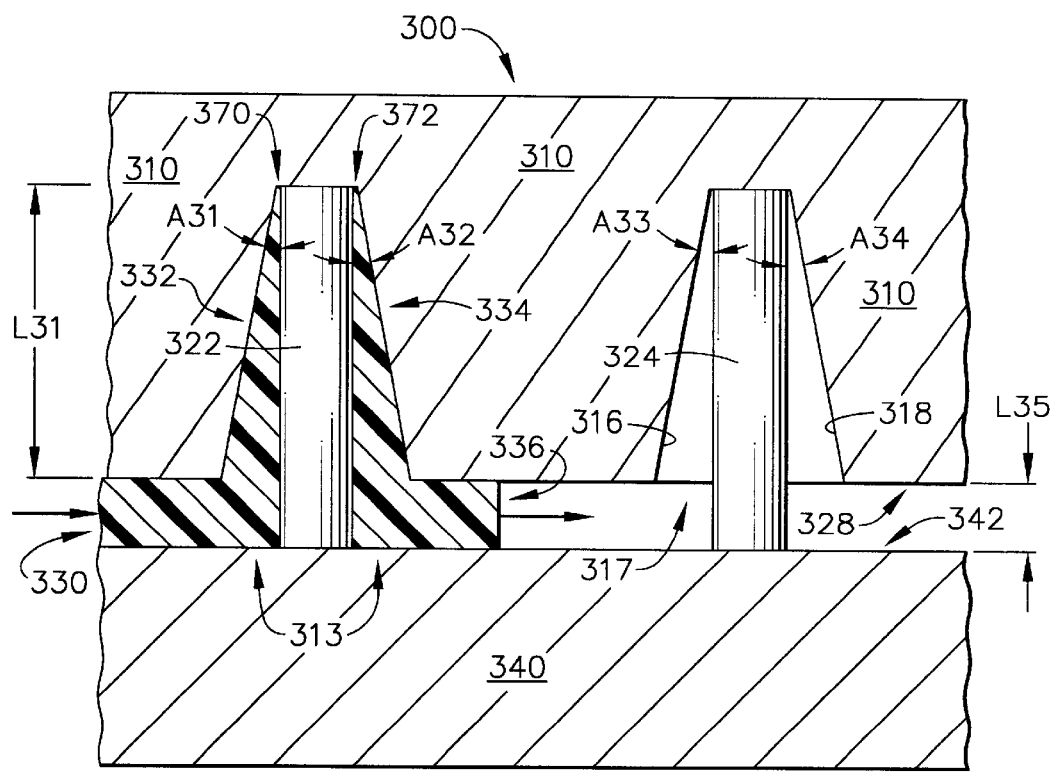
FIG. 16 is an elevational view in partial cross-section of a two-piece mold used in a microinjection method of manufacturing plastic microneedles, as constructed according to the principles of the present invention.

Referring to FIG. 16, a mold 300 consists of two mold-halves 310 and 340. These mold-halves 310 and 340 are virtually identical in shape, and probably in size, as compared to the mold-halves 210 and 240 of the mold 200 on FIG. 12. The main difference in FIG. 16 is that these mold-halves are to be used in a microinjection procedure in which molten plastic material is injected from the side at 330 into the opening between the mold-halves formed by the bottom surface 328 of the top mold-half 310 and the top surface 342 of the bottom mold-half 340.

The mold structure 300 is preferably made of a metallic material by a micro-machining process, although it could be made of a semiconductor material such as silicon or silicon carbide, if desired. On FIG. 16, the plastic material 330 is being filled from the left-hand side in this view, and has already filled a first microhole 313 with plastic material. The plastic material is illustrated as it is advancing, and has reached the point at the reference numeral 336. As time proceeds, the plastic material will reach and fill the second microhole 317, which has a conical inner wall at 316 and 318, and a corresponding micropillar 324.

At the first microhole 313, the plastic material has filled the shape around a micropillar 322 and within the conical walls of this microhole 313, to form a hollow cone having an outer wall at 332 and 334. The plastic material will be forced upward until it reaches a top point as seen at the reference numerals 370 and 372. The outer conical shape at 332 and 334 will converge with the interior shape of the micropillar 322 at an angle designated by the angles "A31" and "A32." Microhole 317 also exhibits a converging angular shape at "A33" and "A34," which is the convergence angle between the conical walls 316 and 318 and the outer cylindrical shape of the micropillar 324.

The separation between the surfaces 328 and 342 is given by the length dimension "L35," which will become the thickness of the planar face material that will remain once the mold is opened. The vertical dimension (in FIG. 16) of the microholes is given by the dimension "L31" which preferably will create microneedles long enough to penetrate through the stratum corneum and into the epidermis, but not so long as to penetrate all the way to the dermis.

Figure 17:
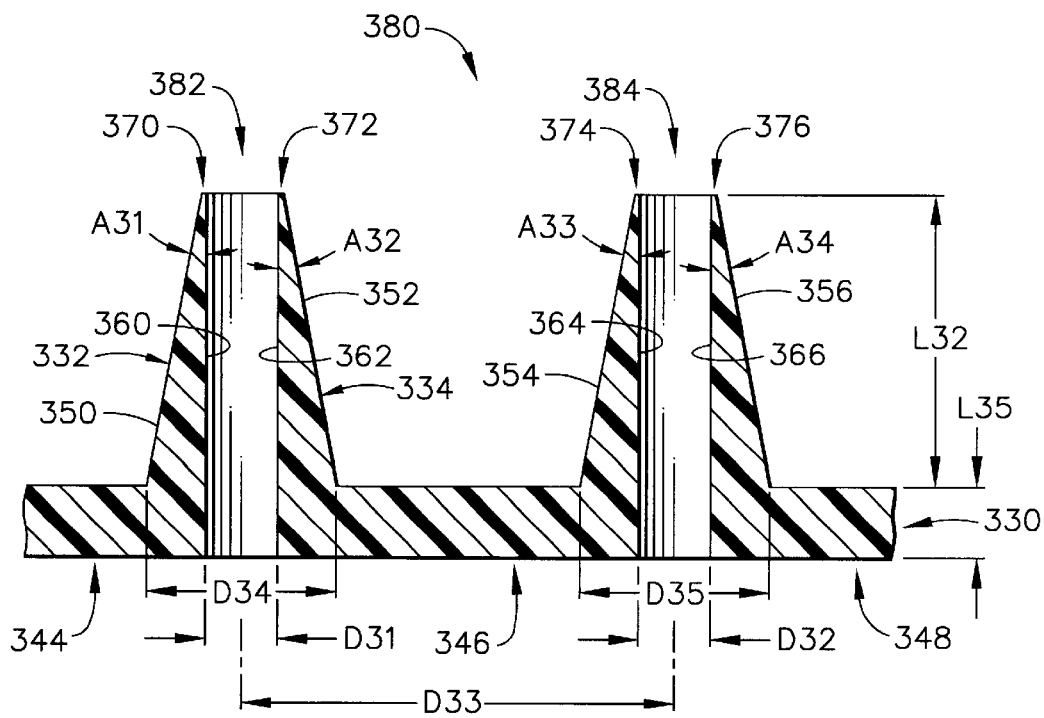
FIG. 17 is a cross-sectional view of a microneedle array of hollow microneedles constructed by the mold of FIG. 16.

FIG. 17 illustrates the microneedle array, generally designated by the reference numeral 380. On FIG. 17, two microneedles are illustrated at 382 and 384. These microneedles have a length "L32," which in theory should be exactly the same as the dimension L31 on FIG. 16, assuming the mold was properly filled with material. A preferred distance for L32 is in the range of 50–200 microns.

The plastic material 330 has a planar base structure, as illustrated at 344, 346, and 348. The thickness of this base structure is the dimension L35. The microneedles themselves exhibit a conical outer wall at 350 and 352 for the left-hand microneedle 382, and at 354 and 356 for the right-hand microneedle at 384. Each microneedle has a hollow interior, as illustrated by the cylindrical surface 360 and 362 for microneedle 382, and 364 and 366 for microneedle 384. These surfaces converge to form points (as illustrated on FIG. 17) at 370 and 372 for microneedle 382, and at 374 and 376 for microneedle 384. The convergence angle of these walls is designated by the angles A31–A34, and preferably will be in the range of zero (0) to forty-five (45) degrees.

The inner diameter of microneedle 382 is given by the dimension D31, and for microneedle 384 is given by dimension D32. These dimensions preferably are in the range 1–49, more preferably about 10 microns. The separation distance between the center lines of the microneedles is given at D33, which preferably is in the range 50–1000 microns, more preferably about 200 microns. The height L32 is preferably in the range of 50–200 microns and, depending upon the convergence angle A31–A34, the bottom width of the conical microneedles will vary depending upon the exact application for usage. In one preferred embodiment, this bottom dimension, designated by "D34" and "D35," will be approximately twenty (20) microns. The vertical thickness at L35 will likely be made as thin as possible, however, the important criterion is that it is sufficiently thick to be mechanically sound to hold the microneedle array 380 together as a single structure during actual usage. It is likely that, for most plastic materials that might be used in this molding procedure, the dimension L35 will be in the range of ten (10) microns through two (2) mm, or greater.

Figure 21:
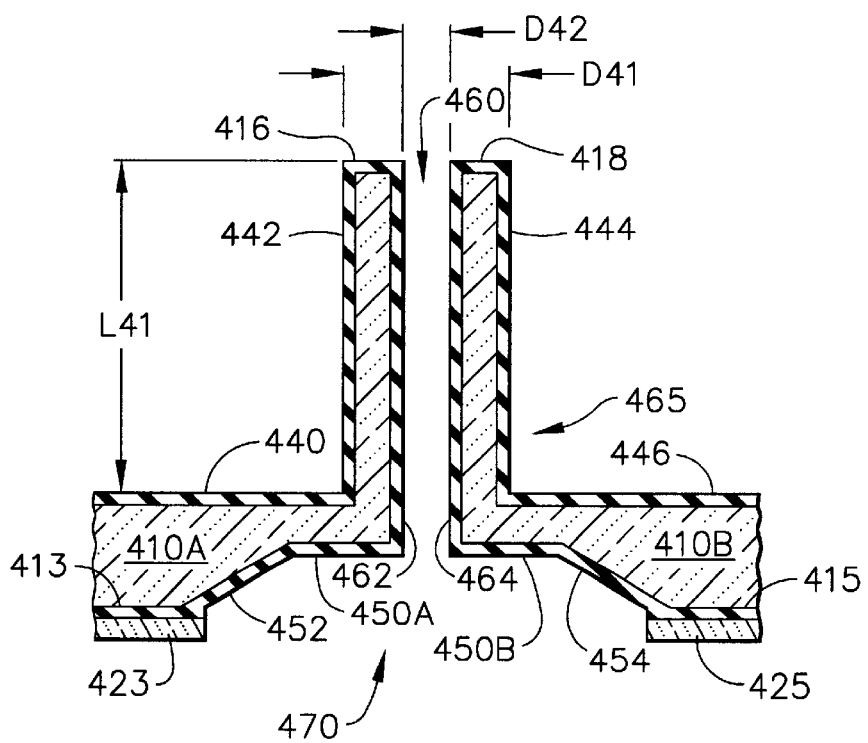
FIG. 21 is a cross-sectional view of the wafer of FIG. 20 after the silicon nitride has been removed, and after a deep reactive ion etch has created through holes, thereby resulting in a hollow microneedle.

The angular relationship between the microneedles and the corresponding planar base surface is preferably perpendicular, although an exact right angle of 90 degrees is not required. This applies to all microneedle embodiments herein described, including microneedles 62, 64 and planar surfaces 30, 32, 34 of FIG. 6, microneedles 182, 184 and planar surfaces 140, 142, 144 of FIG. 11, microneedles 282, 284 and planar surfaces 244, 246, 248 of FIG. 15, microneedles 292, 294 and planar surfaces 244, 246, 248 of FIG. 15A, microneedles 382, 384 and planar surfaces 344, 346, 348 of FIG. 17, and microneedle 470 and planar surfaces 440, 446 of FIG. 21.

It will be understood that other methods of forming plastic microneedles could be utilized to create hollow microneedles in an array, without departing from the principles of the present invention. It will also be understood that various types of materials could be used for such molding procedures, including metallic materials that might be cast using higher temperature dies of a similar shape and size, without departing from the principles of the present invention.

It will be further understood that variations in dimensions and angular relationships could be utilized to construct an array of hollow microneedles, without departing from the principles of the present invention. It will be still further understood that the angular relationship between the microneedles and their planar base surface need not be precisely perpendicular (although that configuration is preferred), but could have some variation without departing from the principles of the present invention; the microneedles also need not be exactly parallel with one another, even though that configuration is preferred.

It will be yet further understood that other microneedle shapes could be used than a cylindrical shape, if desired, without departing from the principles of the present invention. Moreover, it will be understood that, with only simple modifications to the molds, an array of solid microneedles could be fabricated using the molding techniques described herein, without departing from the principles of the present invention.

While there are conventional hollow needles that can be arranged in an array, such conventional needles are all much larger in both length and diameter than those disclosed hereinabove, and therefore, will penetrate all the way into the dermal layer, thereby inflicting a certain amount of pain to the user. Moreover, these larger needles can be made using more conventional manufacturing techniques, since their dimensions will allow for a relaxed standard of manufacture.

Figure 18:
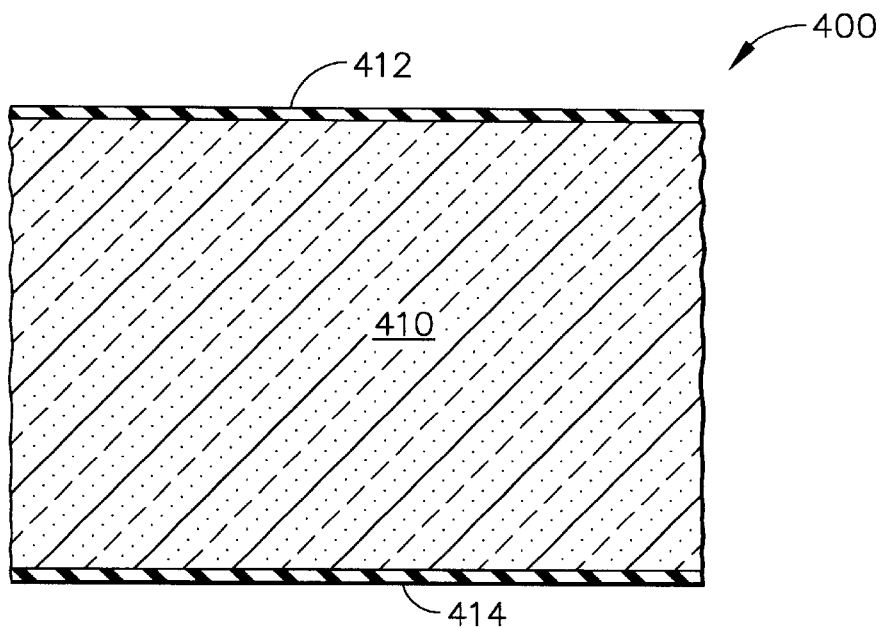
FIG. 18 is a cross-sectional view of the initial semiconductor wafer that will be formed into an array of microneedles by a microfabrication procedure, according to the principles of the present invention.

Referring now to FIG. 18, a procedure for forming dry etched microneedles will be described using an example of microfabrication (e.g., semiconductor fabrication) techniques. Starting with a single crystal silicon wafer at reference numeral 400, it is preferred to use a double side polish wafer and to grow an oxide layer on the entire outer surface. In FIG. 18, a cross-section of this wafer appears as a substrate 410, a top oxide layer 412, and a bottom oxide layer 414. Any single crystal silicon wafer will suffice, although it is preferred to use a crystal structure 100-type wafer, for reasons that will be explained below. A 110-type wafer could be used, however, it would create different angles at certain etching steps.

To create the structure depicted in FIG. 19, certain process steps must first be performed, as described below. The first step is a pattern oxide step which is performed on the top side only to remove much of the top oxide layer 412. The pattern used will create multiple annular regions comprising two concentric circles each, of which the cross-section will appear as the rectangles 416 and 418 on FIG. 19. In perspective, these annular-shaped features will have the appearance as illustrated on the perspective view of FIG. 22 at the reference numerals 416 and 418. These annular oxide patterns are the initial stages of the array locations of the multiple microneedles that will be formed on this substrate 410.

The next step is to deposit a layer of silicon nitride using a low pressure vapor deposition step, which will form a silicon nitride layer on both the top and bottom surfaces of the substrate 410. This appears as the uppermost layer 420 and the bottom most layer 422 and 424. It will be understood that the bottom most layer 422 and 424 is one continuous layer at this step, although it is not illustrated as such on FIG. 19, since a later step etches out a portion of the bottom side of the substrate between the layers 422 and 424.

Figure 19:
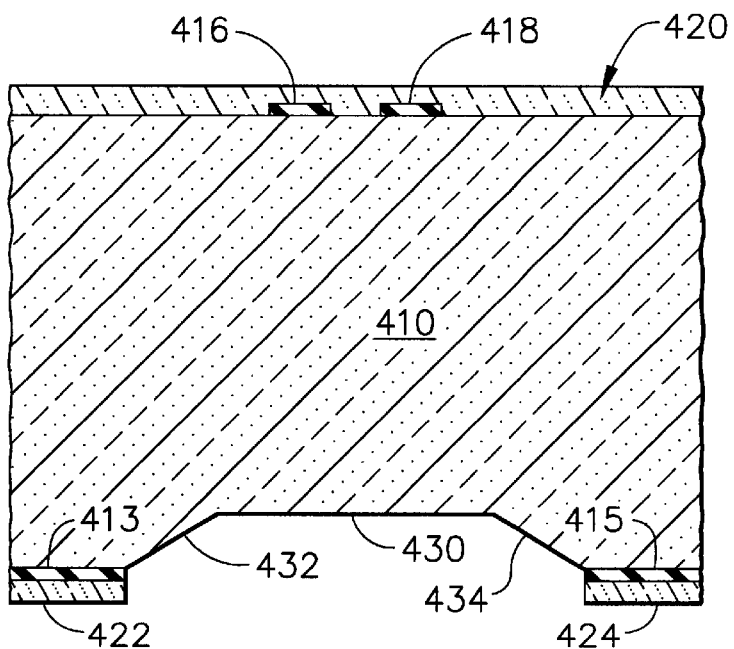
FIG. 19 is a cross-sectional view of the semiconductor wafer of FIG. 18 after a hole pattern has been established, and after a silicon nitride layer has been deposited.

Next in the process is a pattern bottom procedure in which a square hole is patterned beneath the annulus 416, 418, which is not directly visible on FIG. 19. The square holes placed by the pattern bottom procedure are now used in a KOH etching step that is applied to the bottom side only of the substrate 410. This KOH etching step creates a window along the bottom of the substrate as viewed along the surfaces 432, 430, and 434 on FIG. 19. This window interrupts the oxide layer 414 along the bottom of substrate 410, and divides it (on FIG. 19) into two segments 413 and 415. This window (or hole) also interrupts the silicon nitride layer into two segments (on FIG. 19) 422 and 424.

The slope angle of the etched window along surfaces 432 and 434 is 54.7 degrees, due to the preferred 100-type silicon material. If type-110 silicon material was used, then this slope would be 90 degrees. That would be fine, however, crystalline silicon 100-type material is less expensive than silicon 110-type material. After the KOH time etching step has been completed, the silicon wafer will have the appearance as depicted in FIG. 19.

The next fabrication operation is to perform a pattern top nitride procedure using a photoresist mask. This removes the entire upper silicon nitride layer 420 except where the photoresist mask was located, which happens to be aligned with the upper oxide annulus at 416 and 418. The remaining upper silicon nitride is indicated at the reference numeral 426 on FIG. 20, although at this stage in the fabrication procedure, the upper surface will still be a planar surface at the level of the oxide layer 416 and 418, across the entire horizontal dimension of FIG. 20.

The next fabrication step is to perform a deep reactive ion etch (DRIE) operation on the top surface of the substrate 410, which will etch away a relatively deep portion of the upper substrate except at locations where the silicon nitride layer still remains, i.e., at 426. In this DRIE procedure, it is preferred to remove approximately 50–70 microns of material. After that has occurred, the remaining photoresist mask material is removed. This now exposes the top silicon nitride layer 426.

The next fabrication step is to oxidize all of the bare silicon that is now exposed along the outer surfaces. This will form a layer of silicon dioxide at locations on FIG. 20, such as at 440, 442, 444, 446, 452, 450, and 454. The outer silicon nitride layers at 426, 423, and 425 are not oxidized. The outer silicon nitride layers 423 and 425 are essentially the same structures as layers 422 and 424 on FIG. 19, although the silicon dioxide layers 452 and 454 are now formed above these "pads" 423 and 425. It is preferred that this oxidation be a minimal amount, just enough for a future DRIE masking procedure, and that the oxidized thickness be approximately 5,000 Angstroms. At this point in the fabrication procedure, the silicon wafer has the appearance of that depicted in FIG. 20.

Figure 20:
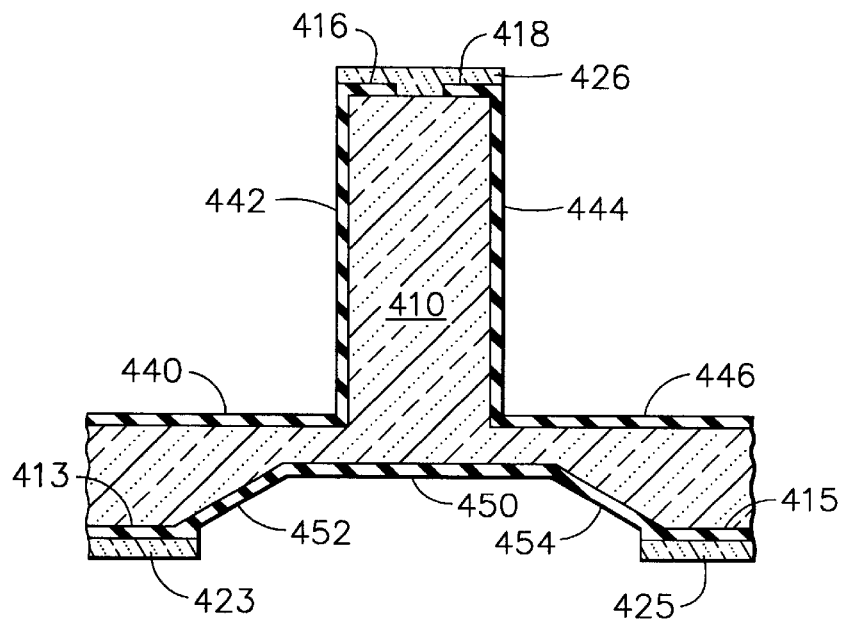
FIG. 20 is a cross-sectional view of the wafer of FIG. 18 after a photoresist mask operation, a deep reactive ion etch operation, and an oxidize operation have been performed.

The next step in the fabrication procedure is to remove the silicon nitride layer on the top, which will remove the layer at 426 as seen on FIG. 20. This will expose a circular region in the very center of the annulus such that pure silicon is now the outermost material on the top side of the wafer. After that has occurred, a deep reactive ion etch operation is performed to create a through-hole at the reference numeral 460 on FIG. 21. After this step has been performed, there will be pure silicon exposed as the inner wall of the through-hole 460. Therefore, the next step is to oxidize the entire wafer, which will place a thin cylindrical shell of silicon dioxide around the inner diameter of through-hole 460, and this oxidized layer is viewed on FIG. 21 at 462 and 464.

After these steps have been performed, a microneedle 465 is the result, having an outer diameter at "D41," and an inner diameter through-hole at "D42." It is preferred that the inner diameter D42 have a distance in the range of 5–10 microns. The height of the microneedle is given at the dimension "L41," which has a preferred dimension in the range of 50–200 microns. On FIG. 21, the substrate 410 has been divided into halves at 410A and 410B. In addition, the bottom oxide layer 450 has been divided in halves at 450A and 450B.

The bottom chamber formed by the sloped surfaces 452 and 454, in combination with the horizontal surfaces 450A and 450B, act as a small, recessed storage tank or chamber generally indicated by the reference numeral 470. This chamber 470 can be used to store a fluid, such as insulin, that is to be dispensed through the cylindrical opening 460 in the hollow microneedle 465. At the scale of FIG. 21, this chamber is not very large in overall physical volume, and it normally would be preferred to interconnect all of such chambers for each of the microneedles in the overall array so that a common fluid source could be used to dispense fluid to each of these chambers 470. Furthermore, there may be a need to dispense a physically much larger volume of fluid, and it also may be desirable to provide a pressure source, such as a pump. In such situations, it may be preferable to have an external storage tank that is in communication with each of the fluid chambers 470 on the wafer that is used to make up the array of microneedles, such as microneedle 465.

Figure 22:
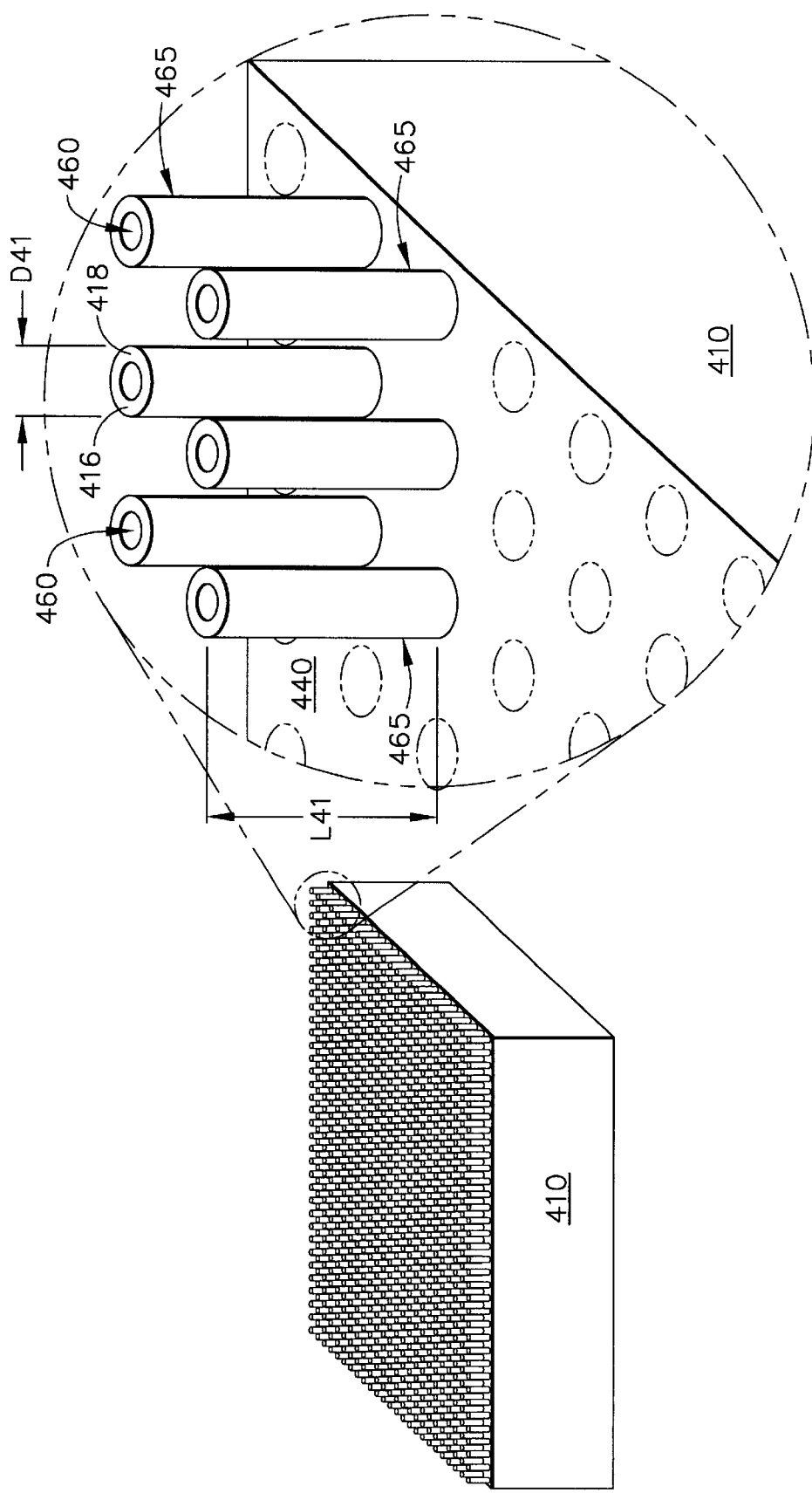
FIG. 22 is a perspective view of a microneedle array on a semiconductor substrate, including a magnified view of individual cylindrical microneedles.

FIG. 22 depicts an array of microneedles on substrate 410, and also illustrates a magnified view of some of these microneedles 465. Each microneedle 465 exhibits a cylindrical shape in the vertical direction, and has an outer diameter D41, an annular shaped upper surface at 416 and 418, and a through-hole at 460. Each of the microneedles 465 extends out from the planar surface 440 of the substrate 410.

As can be seen in FIG. 22, substrate 410 can either be made much larger in height so as to have a very large internal volume for holding a fluid substance, or the substrate itself could be mounted onto a different material that has some type of fluidic opening that is in communication with the chambers 470 of the individual microneedles 465.

It will be understood that other semiconductor substances besides silicon could be used for the fabrication of the array of microneedles depicted on FIG. 22, without departing from the principles of the present invention. Moreover, other microneedle shapes could be used than a cylindrical shape with an annular top surface, and in fact, the top surface of such microneedles could be sloped to create a sharper edge, if desired, without departing from the principles of the present invention.

It will also be understood that the preferred dimensions discussed hereinabove are only preferred, and any microneedle length or diameter that is appropriate for a particular chemical fluidic compound and for a particular skin structure could be used without departing from the principles of the present invention. As discussed above, it is preferred that the microneedle penetrate through the stratum corneum into the epidermis, but not penetrate into the dermis itself. This means that such microneedles would typically be no longer than two hundred (200) microns, though they must typically be at least fifty (50) microns in length. Of course, if cosmetic applications were desired, then the microneedle could be much shorter in length, even as short as one (1) micron. Finally, it will be understood that any size or shape of fluid-holding chamber could be used in a drug-delivery system, which will be further discussed hereinbelow. In addition, for a body-fluid sampling system, a fluid-holding chamber would also preferably be in communication with the through-holes 460 of each of the microneedles 465.

Figure 23:
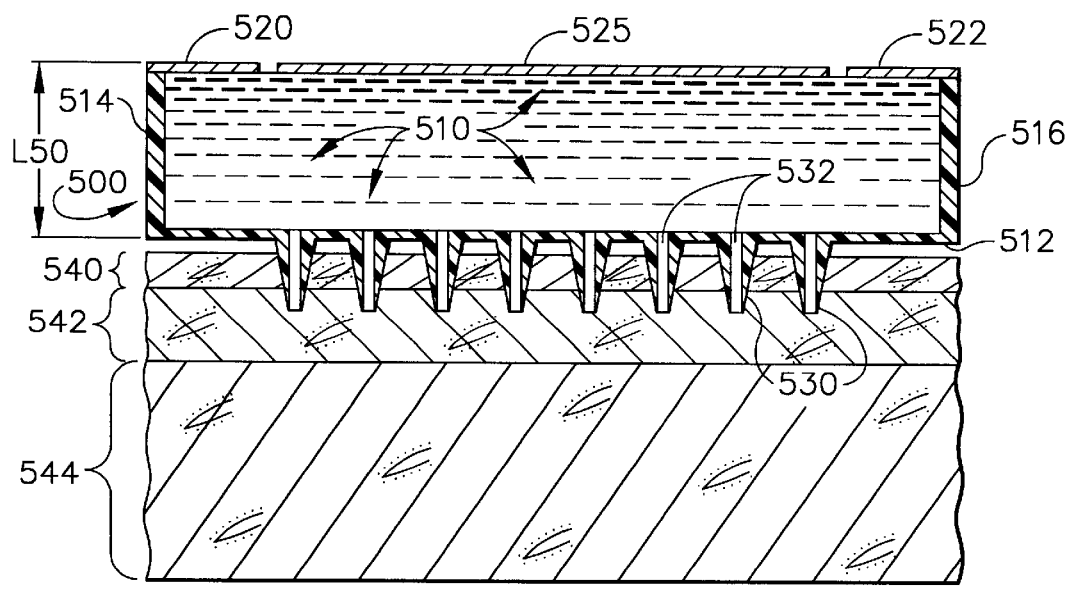
FIG. 23 is a cross-sectional view of an iontophoretically enhanced body-fluid sensor, based upon a hollow microneedle array, as constructed according to the principles of the present invention.

FIG. 23 depicts an iontophoretically enhanced body-fluid sensor that is based upon a hollow microneedle array, generally designated by the reference numeral 500. Sensor 500 includes a plurality of microneedles 530, which are each hollow, having a vertical opening throughout, as indicated at 532. A fluid chamber 510 is in communication with the hollow portions 532 of the array of microneedles 530.

Fluid chamber 510 is constructed of a bottom (in FIG. 23) planar surface 512—which has openings that are aligned with the microneedles 530—a left vertical wall 514, and a right vertical wall 516. The top (or ceiling) of the fluid chamber 510 is made up of a planar material which is divided into individual electrodes. The middle electrode 525 is part of the fluid sensor, and makes it possible to measure a current or voltage within the fluid chamber 510. Electrodes 520 and 522 are electrically connected to one another (and can be of a single structure, such as an annular ring) so as to act as the iontophoretic electrodes (i.e., as either an anode or a cathode) that facilitate the transport of fluid through the hollow microneedles 530 from the skin into the fluid chamber 510.

The height of the fluid chamber structure is designated as "L50," which could be any reasonable dimension that is large enough to hold a sufficient volume of fluid for a particular application. Of course, if desired, the fluid chamber 510 could be connected to a much larger external reservoir (not shown), and a pump could even be used if pressure or vacuum is desired for a particular application.

The layer 540 represents the stratum corneum, the layer 542 represents the viable epidermis, and the largest layer 544 represents the dermis, which contains nerves and capillaries.

The application of microneedles 530 into the stratum corneum 540 and epidermis 542 decreases the electrical resistance of the stratum corneum by a factor of approximately fifty (50). The applied voltage, therefore, during iontophoresis can be greatly reduced, thereby resulting in low power consumption and improved safety. Iontophoresis provides the necessary means for molecules to travel through the thicker dermis into or from the body. The combination of the microneedles and the electric field that is applied between the electrodes 520 and 522 (acting as an anode, for example) and a remotely placed electrode (e.g., electrode assembly 505, viewed on FIG. 25, and acting as a cathode, for example) provides for an increase in permeability for both the stratum corneum and the deeper layers of skin.

While the transport improvement in stratum corneum is mostly due to microneedle piercing, the iontophoresis provides higher transport rates in the epidermis and dermis. This is not only true for small sized molecules, but also for the larger and more complex useful molecules.

The body-fluid sampling sensor 500 can be used for a continuous non-invasive measurement of blood glucose level, for example. Glucose is extracted through the skin by reverse iontophoresis, and its concentration is then characterized by a bioelectrochemical sensor. The sensor comprises the chamber 510 that is filled with hydrogel and glucose oxidase, and the electrode 525. The glucose molecules are moved from the body by the flow of sodium and chloride ions caused by the applied electric potential. The detection of the glucose concentration in the hydrogel pad is performed by the bioelectrochemical sensor.

Figure 24:
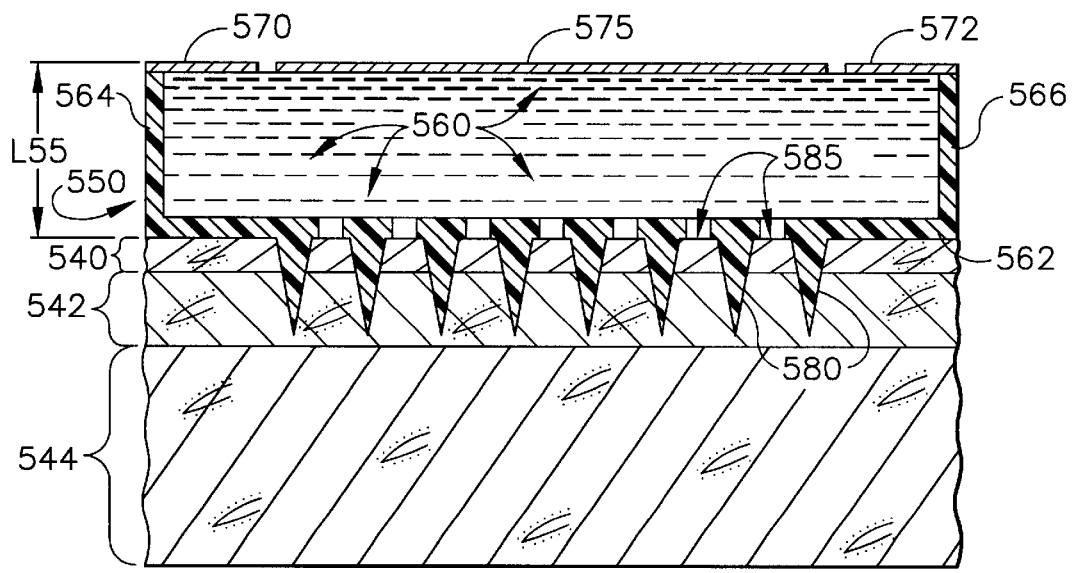
FIG. 24 is a cross-sectional view of an iontophoretically enhanced body-fluid sensor, based upon a solid microneedle array, as constructed according to the principles of the present invention.

An alternative embodiment 550 is depicted in FIG. 24, in which the microneedles 580 are solid, rather than hollow. A fluid-filled chamber 560 is provided and also comprises hydrogel filled with glucose oxidase. The chamber 560 is made of a bottom wall 562 that has openings proximal to the individual microneedles 580, in which these openings are designated by the reference numeral 585. Chamber 560 also includes side walls 564 and 566, as well as electrodes 570, 572, and 575.

The electrode 575 is constructed as part of the bioelectrochemical sensor. The electrodes 570 and 572 act as the iontophoretic electrodes, acting either as an anode or cathode to set up an electric current through the skin which flows to a remotely-attached (to the skin) electrode (e.g., electrode assembly 555, viewed on FIG. 26).

As in the sensor 500 of FIG. 23, the transport rate of fluids is enhanced by not only the piercing effect of the microneedles 580, but also the electric field inducing a current through the skin. In the glucose sampling example, glucose is attracted into the chamber 560, and its concentration is measured by the bioelectrochemical sensor.

The height of the fluid chamber structure is designated as "L55," which could be any reasonable dimension that is large enough to hold a sufficient volume of fluid for a particular application. Of course, if desired, the fluid chamber 560 could be connected to a much larger external reservoir (not shown), and a pump could even be used if pressure or vacuum is desired for a particular application.

Figure 25:
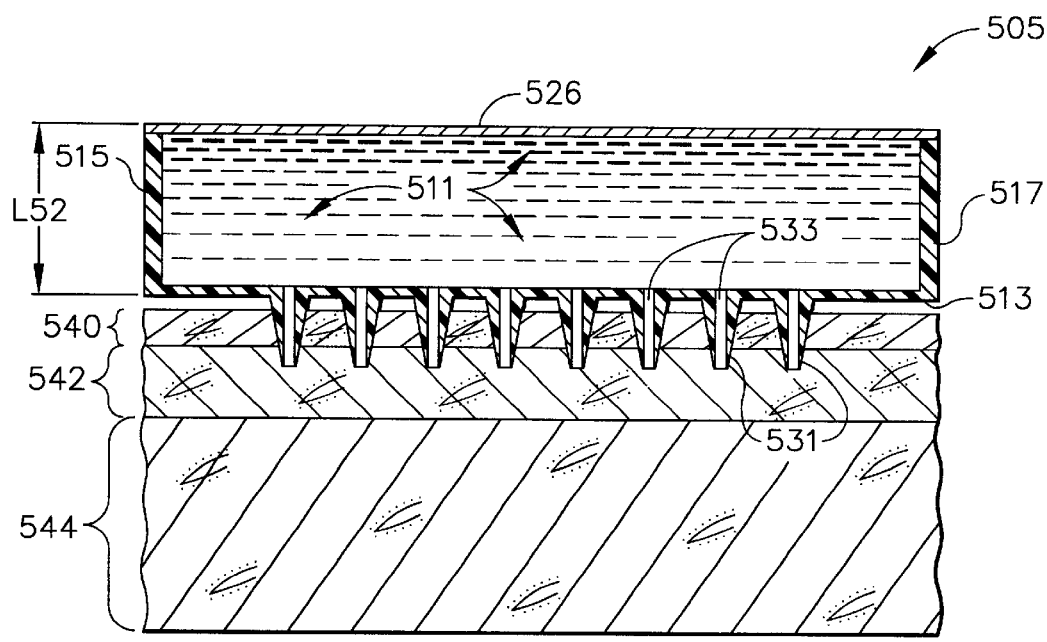
FIG. 25 is a cross-sectional view of an electrode, based upon a hollow microneedle array, as constructed according to the principles of the present invention.

FIG. 25 depicts an iontophoretic electrode assembly that is based upon a hollow microneedle array, generally designated by the reference numeral 505. Electrode assembly 505 includes a plurality of microneedles 531, each being hollow and having a vertical opening throughout, as indicated at 533. A fluid chamber 511 is in communication with the hollow portions 533 of the array of microneedles 531.

Fluid chamber 511 is constructed of a bottom planar surface 513—which has openings that are aligned with the microneedles 531-a left vertical wall 515, and a right vertical wall 517. The top (or ceiling) of fluid chamber 511 is made of a planar electrode material 526. The electrode 526 is to be electrically connected to a low-current voltage source (not shown on FIG. 25), either through a substrate pathway (such as a integrated circuit trace or a printed circuit foil path) or a wire (also not shown on FIG. 25).

The height of the fluid chamber 511 is given by the dimension "L52," which can be of any practical size to hold a sufficient amount of hydrogel, for example, to aid in the conduction of current while acting as the electrode. In electrode assembly 505, the fluid within chamber 511 preferably would not be electrically charged.

As can be seen in FIG. 25, the hollow microneedles 531 penetrate the stratum corneum 540 and into the viable epidermis 542. The microneedles 531 preferably will not be sufficiently long to penetrate all the way to the dennis 544.

Figure 26:
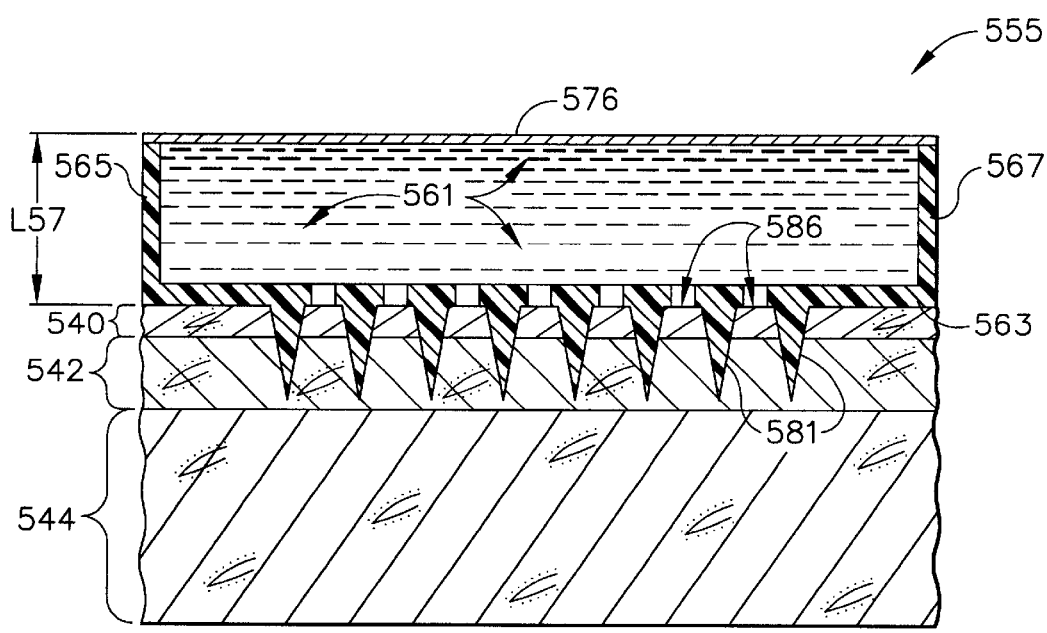
FIG. 26 is a cross-sectional view of an electrode, based upon a solid microneedle array, as constructed according to the principles of the present invention.

An alternative embodiment 555 is depicted in FIG. 26, in which the microneedles 581 are solid, rather than hollow. A fluid chamber 561 is provided and preferably is filled with hydrogel (which is not electrically charged). Chamber 561 is made of a bottom wall 563 that has openings proximal to the individual microneedles 581, in which these openings are designated by the reference numeral 586. Chamber 561 also includes side walls 565 and 567, as well as a top (or ceiling) electrode 576. The electrode 576 may act as a cathode, for example, in a situation where electrode assembly 555 is being used in conjunction with a body-fluid sensor, such as sensor assembly 550 viewed on FIG. 24, in which its electrodes 570 and 572 may act, for example, as an anode. The height "LS7" of fluid chamber 561 could be any reasonable dimension that is large enough to hold a sufficient volume of the hydrogel to enhance the fluid flow via the electric field between the respective anode and cathode of the system.

Figure 27:
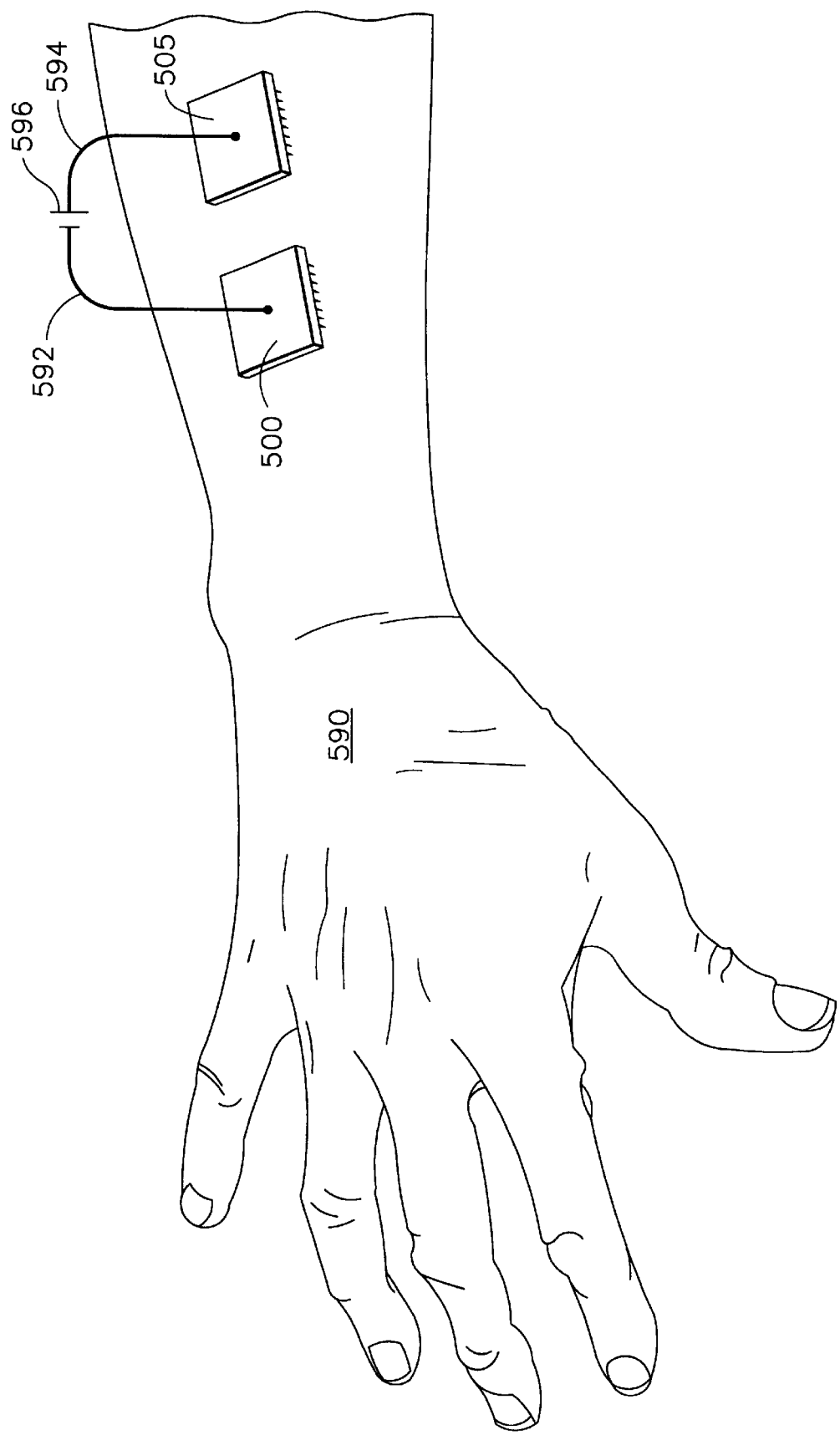
FIG. 27 is a perspective view of a sensing system attached to a human hand and forearm, which includes an iontophoretically enhanced body-fluid sensor as per FIG. 23 and an electrode as per FIG. 25.

FIG. 27 illustrates a portion of a human arm and hand 590, along with a drug delivery electrode assembly 500 and a second electrode assembly 505. Both electrodes are attached to the skin of the human user, via their microneedles, such as the hollow microneedles 530 (viewed on FIG. 23) and the hollow microneedles 531 (viewed on FIG. 25).

Since an electrical voltage is applied between the two electrode assemblies 500 and 505, it is preferred to use a low current power supply, generally designated by the reference numeral 596, that is connected to each of the electrodes via a wire 592 or a wire 594, respectively. It will be understood that any type of physical electrical circuit could be used to provide the electrical conductors and power supply necessary to set up an appropriate electrical potential, without departing from the principles of the present invention. In fact, the electrode assemblies and wiring, along with an associated power supply, could all be contained on a single apparatus within a substrate, such as that viewed on FIGS. 30 and 31 herein, or by use of printed circuit boards.

Figure 28:
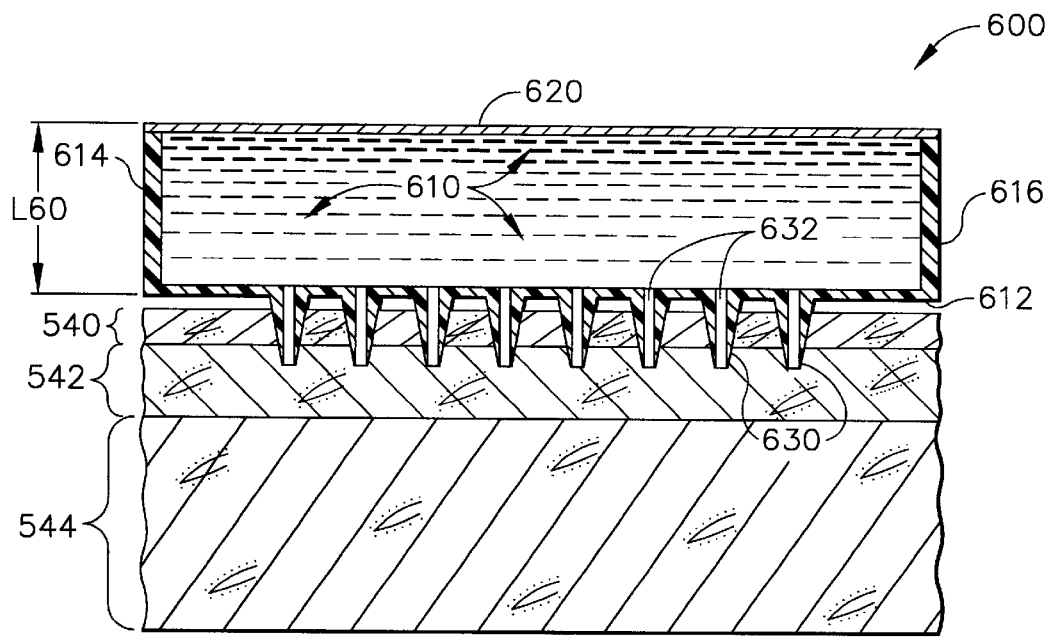
FIG. 28 is a cross-sectional view of an iontophoretically enhanced drug delivery system, based upon a hollow microneedle array, as constructed according to the principles of the present invention.

FIG. 28 depicts an iontophoretically enhanced fluidic drug delivery apparatus that is based upon a hollow microneedle array, generally designated by the reference numeral 600. Drug-delivery apparatus 600 includes a plurality of microneedles 630, which are each hollow, having a vertical opening throughout, as indicated at 632. A fluid chamber 610 is in communication with the hollow portions 632 of the array of microneedles 630.

Fluid chamber 610 is constructed of a bottom (in FIG. 28) planar surface 612—which has openings that are aligned with the microneedles 630—a left vertical wall 614, and a right vertical wall 616. The top (or ceiling) of the fluid chamber 610 is made up of a planar material 620 that acts as an electrode. Electrode 620 is part of the drug delivery apparatus, and makes it possible to induce a current flow through fluid chamber 610. Electrodes 620 and 622 are connected so as to act as the iontophoretic electrodes (i.e., as either an anode or a cathode) that facilitate the transport of fluid through the hollow microneedles 630 from the fluid chamber 610 into the skin.

The height of the fluid chamber structure is designated as "L60," which could be any reasonable dimension that is large enough to hold a sufficient volume of fluid for a particular drug delivery application. Of course, if desired, the fluid chamber 510 could be connected to a much larger external reservoir (not shown), and a pump could even be used if pressure or vacuum is desired for a particular application.

The layer 540 represents the stratwn corneum, the layer 542 represents the viable epidermis, and the largest layer 544 represents the dermis, which contains nerves and capillaries.

The application of microneedles 630 into the stratum corneum 540 and epidermis 542 decreases the electrical resistance of the stratum corneum by a factor of approximately fifty (50). The applied voltage, therefore, during iontophoresis can be greatly reduced, thereby resulting in low power consumption and improved safety. Iontophoresis provides the necessary means for molecules to travel through the thicker dermis into or from the body. The combination of the microneedles and the electric field that is applied between the electrodes 620 and 622 (acting as anodes, for example), and another electrode (e.g., electrode assembly 505, acting as a cathode) that is attached elsewhere on the skin of the user, provides for an increase in permeability for both the stratum comeum and the deeper layers of skin. While the transport improvement in stratum corneum is mostly due to microneedle piercing, the iontophoresis provides higher transport rates in the epidermis and dermis. This is not only true for small sized molecules, but also for the larger and more complex useful molecules.

The drug delivery apparatus 600 can be used for a continuous non-invasive medical device that can continuously deliver a fluidic drug through the skin and into the body. For example, insulin could be delivered to the blood stream via the microneedles 531, through the stratum corneum 540 and epidermis 542, and also into the dermis 544 where the insulin would be absorbed into the capillaries (not shown).

Figure 29:
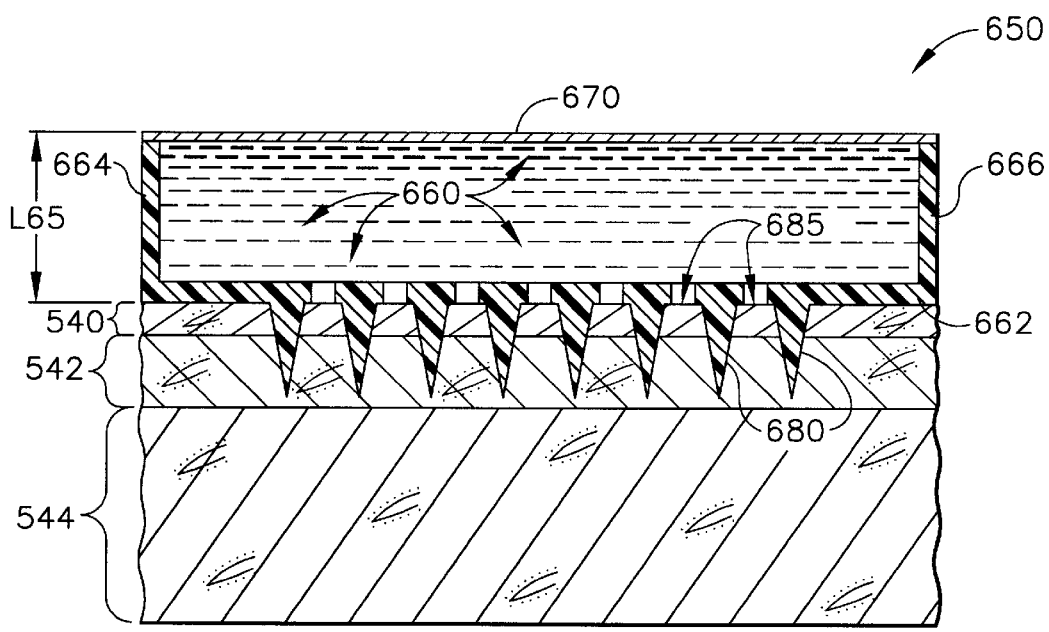
FIG. 29 is a cross-sectional view of an iontophoretically enhanced drug delivery system, based upon a solid microneedle array, as constructed according to the principles of the present invention.

An alternative embodiment 650 is depicted in FIG. 29, in which the microneedles 680 are solid, rather than hollow. A fluid-filled chamber 660 is provided and also contains hydrogel. Chamber 660 is made of a bottom wall 662 that has openings proximal to the individual microneedles 680, in which these openings are designated by the reference numeral 685. Chamber 660 also includes side walls 664 and 666, as well as electrodes 670, 672, and 675.

The electrode 675 is constructed as part of the bioelectrochemical sensor. The electrodes 670 and 672 act as the iontophoretic electrodes, acting either as the anode or cathode to set up an electric current through the skin, in conjunction with another electrode assembly (such as electrode assembly 655, viewed on FIG. 26) placed elsewhere on the user's skin.

As in the drug delivery apparatus 600 of FIG. 28, the transport rate of fluids is enhanced by not only the piercing effect of the microneedles 680, but also the electric field inducing a current through the skin. In the insulin dispensing example, insulin is repelled from the chamber 660, and therefore, flows out through openings 685 proximal to microneedles 680, then into the user's skin.

The height of the fluid chamber structure is designated as "L65," which could be any reasonable dimension that is large enough to hold a sufficient volume of fluid for a particular application. Of course, if desired, the fluid chamber 660 could be connected to a much larger external reservoir (not shown), and a pump could even be used if pressure or vacuum is desired for a particular application.

Figure 30:
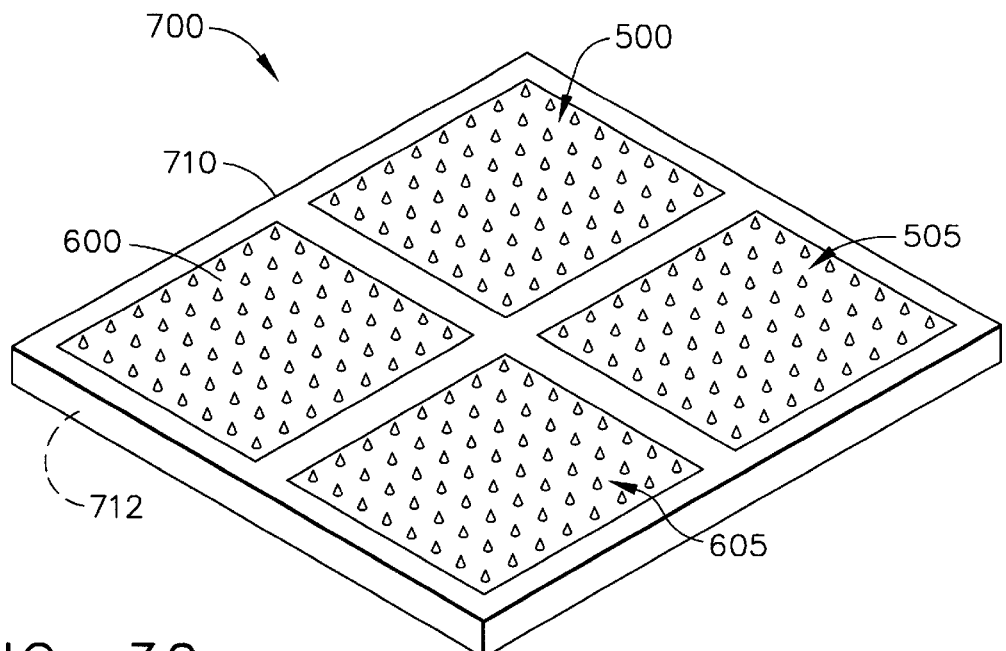
FIG. 30 is a perspective view of a closed-loop drug-delivery system, as viewed from the side of a patch that makes contact with the skin, as constructed according to the principles of the present invention.

FIG. 30 depicts a closed-loop drug-delivery system generally designated by the reference numeral 700. This closed-loop system 700 includes a pair of iontophoretic pads, generally designated by the reference numerals 500 and 505, which each include an array of microneedles for fluid sampling. Pad 500 comprises a sensor assembly (as described hereinabove with respect to FIG. 23), and pad 505 comprises an electrode assembly (as described hereinabove with respect to FIG. 25).

Closed-loop system 700 also includes a pair of iontophoretic pads, generally designated by the reference numerals 600 and 605, that each include an array of microneedles for drug delivery. Pad 600 comprises a drug delivery apparatus (as described hereinabove with respect to FIG. 28), and pad 505 comprises an electrode assembly (as described hereinabove with respect to FIG. 25). Of course, iontophoretic pads having solid microneedles could instead be used, such that pads 500 and 600 (with hollow rnicroneedles) could be replaced by pads 550 and 650 (with solid microneedles), and pad 505 (with hollow microneedles) could be replaced by a pad 555 (with solid microneedles).

Pads 500 and 600 are mounted to a substrate 710, which can be made of either a solid or a somewhat flexible material. Within substrate 710 preferably resides a reservoir 712 (within the substrate 710) that holds the fluid which is to be dispensed through the microneedles of pads 600. Reservoir 712 could be made up of individual "small" chambers, such as a large number of chambers 610 that are connected to a source of fluidic drug.

Figure 31:
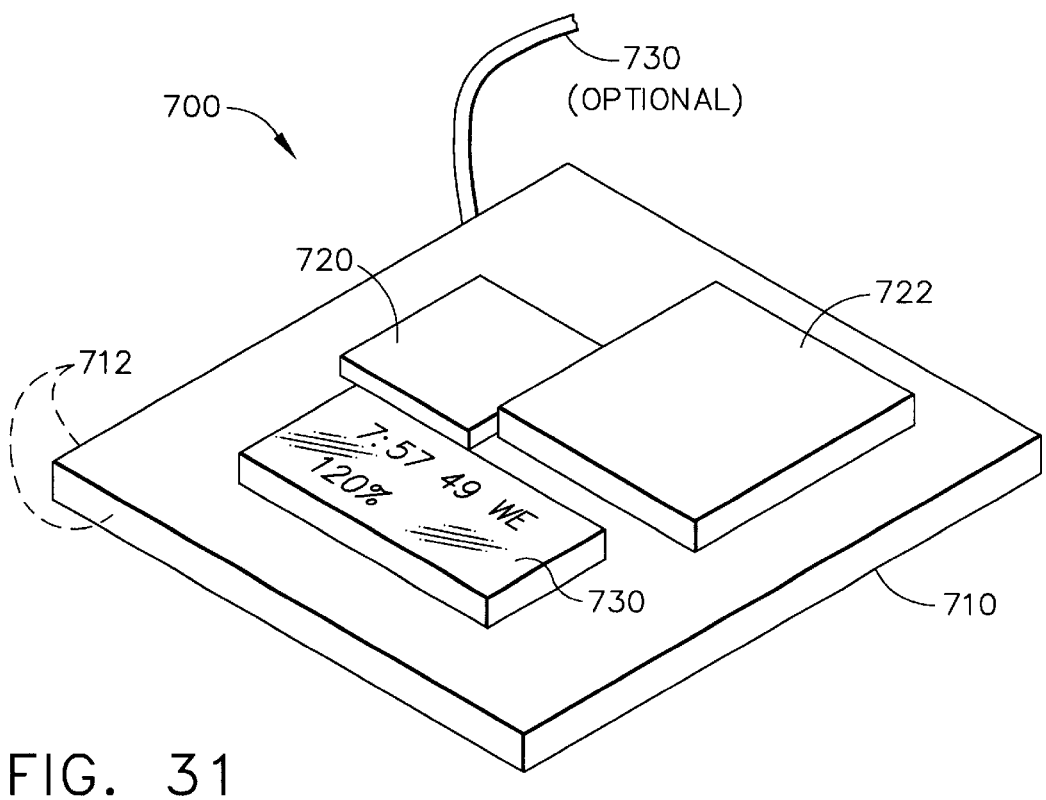
FIG. 31 is a perspective view of the closed-loop drug-delivery system of FIG. 30, as seen from the opposite side of the patch.

It will be understood that the reservoir 712 preferably is completely contained within substrate 710, and cannot be seen from this view of FIG. 31. As an alternative, however, a fluid channel (such as a flexible at 730) could be connected into substrate 710 and, by use of a pump (not shown), further quantities of the fluid could be provided and dispensed through the microneedles of pads 600, using fluidic pressure.

FIG. 31 illustrates the opposite side of the closed-loop system 700. A controller 720 is mounted to the upper surface (in this view) of substrate 710. Controller 720 preferably comprises a type of microchip that contains a central processing unit that can perform numeric calculations and logical operations. A microprocessor that executes software instructions in a sequential (or in a parallel) manner would be sufficient. A microcontroller integrated circuit would also suffice, or an ASIC that contains a microprocessor circuit.

Adjacent to controller 720 is an iontophoretic power supply with a battery, the combination being generally designated by the reference numeral 722. In addition, a visual indicator can be placed on the surface of the substrate, as at 730. This visual indicator could give a direct reading of the quantity of interest, such as glucose concentration, or some other body-fluid parameter. The visual indicator preferably comprises a liquid crystal display that is capable of displaying alphanumeric characters, including numbers.

While a pumping system that creates fluid pressure could be used for dispensing a fluidic drug into a body through hollow microneedles, such as emplaced on pads 600, it is preferred to use an iontophoresis method to enhance the delivery of the drugs through the microneedles. As discussed hereinabove, application of microneedles can decrease the electrical resistance of the stratum comeum by a factor of fifty (50), and so the voltage necessary to facilitate iontophoresis can be greatly reduced, improving safety and requiring much less power consumption. By use of the iontophoresis, the molecules making up the fluid drug will travel through the thicker dermis into or from the body, and the combination of both transport-enhancing methods provides an increase in permeability for both the stratum comeum and the deeper layers of the skin. The transport improvement in the stratum comeum is mostly due to microneedle piercing, although the iontophoresis provides higher transport rates in the epidermis and dermis.

The closed-loop drug-delivery system and fluid-sampling system 700 can be used for continuous noninvasive measurement of blood glucose level by extracting, via reverse iontophoresis, glucose through the skin and measuring its concentration by the bioelectrochemical sensor (such as the sensor constructed of the hydrogel chamber 510 and sensor electrode 525, along with the controller 720). The hydrogel pads containing microneedles (i.e., pads 500) enhance the reverse iontophoresis to move glucose molecules from the body by the flow of sodium and chloride ions, which are caused by the applied electric potential via electrodes 520 and 522. Once the glucose concentration is measured within the hydrogel pads 500, the proper amount of insulin, for example, can be dispensed through the other pair of pads 600 that make up part of the closed-loop system 700.

As discussed hereinabove, drug delivery is performed by applying an electric potential between two microneedle array electrodes. One of the electrodes is filled with an ionized drug (such as insulin), and the charged drug molecules move into the body due to the electric potential. Controller 720 will determine how much of a drug is to be dispensed through the microneedle array 600 at any particular time, thereby making the closed-loop system 700 a "smart" drug-delivery system.

This smart drug-delivery system can be used as an artificial pancreas for diabetes patients, as a portable hormone-therapy device, as a portable system for continuous outpatient chemotherapy, as a site-specific analgesic patch, as a temporary and/or rate-controlled nicotine patch, or for many other types of drugs. Such systems could be made as a disposable design, or as a refillable design.

It will be understood that the closed-loop system 700 can be used in many applications, including as a painless and convenient transdermal drug-delivery system for continuous and controlled outpatient therapies, a painless and convenient body-fluid sampling system for continuous and programmed outpatient body-fluid monitoring, as a high-rate transdermal drug delivery system, or as a high-accuracy transdermal body-fluid sampling system. More specifically, the closed-loop system 700 of the present invention can be used as a portable high-accuracy painless sensor for outpatient blood glucose-level monitoring, as a portable system for continuous or rate controlled outpatient chemotherapy, as a temporary and rate controlled nicotine patch, as a site-specific controlled analgesic patch, as an externally attached artificial pancreas, as externally attached artificial endocrine glands, as temperature-controlled fever-reducing patches, as heart rate-controlled nitroglycerin high-rate transdermal patches, as temporarily controlled hormonal high-rate transdermal patches, as erectile dysfunction treatment high-rate transdermal patches, and as a continuous accurate blood-analysis system. Another use of the closed-loop system 700 of the present invention is to form a portable drug delivery system for outpatient delivery of the following drugs and therapeutic agents, for example: central nervous system therapy agents, psychic energizing drugs, tranquilizers, anticonvulsants, muscle relaxants and anti-parkinson agents, smoking cessation agents, analgetics, antipyretics and anti-inflammatory agents, antispasmodics and antiulcer agents, antimicrobials, antimalarias, sympathomimetric patches, antiparasitic agents, neoplastic agents, nutritional agents, and vitamins.

It will be understood that various materials other than those disclosed hereinabove can be used for constructing the closed-loop system 700, and for constructing individual body-fluid sampling sensors and individual drug-delivery systems. Such other materials could include diamond, biocompatible metals, ceramics, polymers, and polymer composites, including PYREX®. It will yet be further understood that the iontophoretically/microneedle-enhanced transdermal method of transport of the present invention can also be combined with ultrasound and electroporation, in order to achieve high-rate drug delivery into individual cells.

It will also be understood that the length of the individual microneedles is by far the most important dimension with regard to providing a painless and bloodless drug-dispensing system, or a painless and bloodless body-fluids sampling system using the opposite direction of fluid flow. While the dimensions discussed hereinabove are preferred, and the ranges discussed are normal for human skin, it will further be understood that the microneedle arrays of the present invention can be used on skin of any other form of living (or even dead) creatures or organisms, and the preferred dimensions may be quite different as compared to those same dimensions for use with human skin, all without departing from the principles of the present invention.

It yet will be understood that the chemicals and materials used in the molds and dies can be quite different than those discussed hereinabove, without departing from the principles of the present invention. Further, it will be understood that the chemicals used in etching and layering operations of microfabrication discussed above could be quite different than those discussed hereinabove, without departing from the principles of the present invention.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. A method of manufacturing a microneedle array, comprising:
   (a) providing a semiconductor wafer;
   (b) creating a plurality of annular oxide patterns on the top surface of said wafer;
   (c) forming a plurality of indentations in the bottom surface;
   (d) forming, by etching away material, a plurality of needle-like projections in the top surface of said wafer, said needle-like projections having locations that are aligned with said indentations; and
   (e) forming a plurality of through holes in said plurality of needle-like projections, thereby creating an array of hollow microneedles.

2. The method as recited in claim 1, wherein said wafer comprises double side polish (100) silicon, and has an oxide layer on its top surface.

3. The method as recited in claim 1, wherein each of said plurality of hollow microneedles is substantially cylindrical in shape, and each of said through holes is annular.

4. The method as recited in claim 1, wherein the process of creating a plurality of annular oxide patterns on the top surface of said wafer comprises: oxidizing the top surface of said wafer, then performing a pattern oxide operation.

5. The method as recited in claim 1, wherein the process of forming a plurality of indentations in the bottom surface comprises: performing a low pressure vapor nitride deposition operation to form a silicon nitride layer on the bottom surfaces of said wafer, then performing a pattern bottom operation and an etching operation on the bottom surface of said wafer.

6. The method as recited in claim 1, wherein the process of forming a plurality of needle-like projections in the top surface of said wafer comprises: performing a low pressure vapor nitride deposition operation to form a silicon nitride layer on the top surface of said wafer, then performing a pattern top nitride operation and a deep reactive ion etch operation.

7. The method as recited in claim 1, wherein the process of forming a plurality of through holes in said plurality of needle-like projections comprises: removing said top silicon nitride layer, and performing a deep reactive ion etch operation.

\* \* \* \* \*